US011278421B2

(12) United States Patent
Hunt

(10) Patent No.: US 11,278,421 B2
(45) Date of Patent: Mar. 22, 2022

(54) IMPLANT DEVICE HAVING CURVED OR ARCED STRUTS

(71) Applicant: 4WEB, Inc., Frisco, TX (US)

(72) Inventor: Jessee Hunt, Plano, TX (US)

(73) Assignee: 4Web, Inc., Frisco, TX (US)

( * ) Notice: Subject to any disclaimer, the term of this patent is extended or adjusted under 35 U.S.C. 154(b) by 0 days.

(21) Appl. No.: 14/743,607

(22) Filed: Jun. 18, 2015

(65) Prior Publication Data
US 2015/0282946 A1 Oct. 8, 2015

Related U.S. Application Data

(63) Continuation of application No. 12/960,092, filed on Dec. 3, 2010, now Pat. No. 9,421,108, which is a
(Continued)

(51) Int. Cl.
*A61F 2/44* (2006.01)
*A61B 17/16* (2006.01)
(Continued)

(52) U.S. Cl.
CPC ........ *A61F 2/4455* (2013.01); *A61B 17/1604* (2013.01); *A61B 17/56* (2013.01);
(Continued)

(58) Field of Classification Search
CPC .......... A61F 2/4455; A61F 2002/30911; A61F 2002/3092; A61F 2002/30275
(Continued)

(56) References Cited

U.S. PATENT DOCUMENTS 3,840,904 A 10/1974 Tronzo
3,867,728 A 2/1975 Stubstad et al.
(Continued)

FOREIGN PATENT DOCUMENTS

CN 201164511 12/2008
CN 201200499 3/2009
(Continued)

OTHER PUBLICATIONS

International Search Report and Written Opinion for PCT/US2012/063600 dated Jan. 31, 2013.
(Continued)

*Primary Examiner* — Eduardo C Robert
*Assistant Examiner* — Tara Rose E Carter
(74) *Attorney, Agent, or Firm* — Kowert, Hood, Munyon, Rankin & Goetzel, P.C.; Gareth M. Sampson

(57) ABSTRACT

In various embodiments, an implant for interfacing with a bone structure includes a web structure including a space truss. The space truss includes two or more planar truss units having a plurality of struts joined at nodes and the web structure is configured to interface with human bone tissue. In some embodiments, a method is provided that includes accessing an intersomatic space and inserting an implant into the intersomatic space. The implant includes a web structure including a space truss. The space truss includes two or more planar truss units having a plurality of struts joined at nodes and the web structure is configured to interface with human bone tissue.

20 Claims, 27 Drawing Sheets

Related U.S. Application Data continuation of application No. 12/640,825, filed on Dec. 17, 2009, now Pat. No. 8,430,930.

(60) Provisional application No. 61/138,707, filed on Dec. 18, 2008.

(51) Int. Cl.

| | | |
|---|---|---|
| *A61F 2/28* | (2006.01) | |
| *A61F 2/30* | (2006.01) | |
| *A61F 2/38* | (2006.01) | |
| *A61F 2/46* | (2006.01) | |
| *A61F 2/32* | (2006.01) | |
| *A61F 2/40* | (2006.01) | |
| *A61F 2/42* | (2006.01) | |
| *A61B 17/56* | (2006.01) | |
| *A61B 17/58* | (2006.01) | |
| *A61B 17/68* | (2006.01) | |
| *B33Y 70/00* | (2020.01) | |
| *B33Y 80/00* | (2015.01) | |
| *A61B 17/02* | (2006.01) | |
| *A61F 2/36* | (2006.01) | |

(52) U.S. Cl.
CPC .............. *A61B 17/58* (2013.01); *A61B 17/68* (2013.01); *A61F 2/28* (2013.01); *A61F 2/2803* (2013.01); *A61F 2/2846* (2013.01); *A61F 2/30767* (2013.01); *A61F 2/30771* (2013.01); *A61F 2/30907* (2013.01); *A61F 2/32* (2013.01); *A61F 2/38* (2013.01); *A61F 2/40* (2013.01); *A61F 2/4202* (2013.01); *A61F 2/4225* (2013.01); *A61F 2/447* (2013.01); *A61F 2/4611* (2013.01); *A61B 17/025* (2013.01); *A61F 2/3094* (2013.01); *A61F 2/36* (2013.01); *A61F 2002/2817* (2013.01); *A61F 2002/2835* (2013.01); *A61F 2002/3028* (2013.01); *A61F 2002/3092* (2013.01); *A61F 2002/3097* (2013.01); *A61F 2002/30153* (2013.01); *A61F 2002/30156* (2013.01); *A61F 2002/30158* (2013.01); *A61F 2002/30179* (2013.01); *A61F 2002/30273* (2013.01); *A61F 2002/30275* (2013.01); *A61F 2002/30281* (2013.01); *A61F 2002/30593* (2013.01); *A61F 2002/30599* (2013.01); *A61F 2002/30841* (2013.01); *A61F 2002/30899* (2013.01); *A61F 2002/30909* (2013.01); *A61F 2002/30914* (2013.01); *A61F 2002/30943* (2013.01); *A61F 2002/30952* (2013.01); *A61F 2002/30953* (2013.01); *A61F 2002/30957* (2013.01); *A61F 2002/30962* (2013.01); *A61F 2002/30968* (2013.01); *A61F 2002/4628* (2013.01); *A61F 2210/0076* (2013.01); *A61F 2230/0063* (2013.01); *A61F 2310/00011* (2013.01); *A61F 2310/00017* (2013.01); *A61F 2310/00023* (2013.01); *A61F 2310/00029* (2013.01); *A61F 2310/00047* (2013.01); *A61F 2310/0097* (2013.01); *A61F 2310/00179* (2013.01); *A61F 2310/00598* (2013.01); *A61F 2310/00796* (2013.01); *A61F 2310/00958* (2013.01); *A61F 2310/00976* (2013.01); *B33Y 70/00* (2014.12); *B33Y 80/00* (2014.12)

(58) Field of Classification Search
USPC .................... 606/246–249, 62–68, 300–320; 623/17.11–17.16, 20.17
See application file for complete search history.

(56) References Cited

U.S. PATENT DOCUMENTS

| | | | |
|---|---|---|---|
| 4,686,970 A | 8/1987 | Dove et al. | |
| 4,820,305 A | 4/1989 | Harms et al. | |
| 4,904,261 A | 2/1990 | Dove et al. | |
| 4,938,771 A | 7/1990 | Vecsei et al. | |
| 5,030,233 A | 7/1991 | Ducheyne | |
| 5,147,402 A | 9/1992 | Bohler et al. | |
| 5,201,768 A | 4/1993 | Caspari et al. | |
| 5,282,861 A | 2/1994 | Kaplan | |
| 5,336,266 A | 8/1994 | Caspari et al. | |
| 5,433,750 A | 7/1995 | Gradinger et al. | |
| 5,571,185 A | 11/1996 | Schug | |
| 5,609,635 A | 3/1997 | Michelson | |
| 5,609,637 A | 3/1997 | Biedermann et al. | |
| 5,676,700 A | 10/1997 | Black et al. | |
| 5,702,449 A | 12/1997 | McKay | |
| 5,702,451 A | 12/1997 | Biedermann et al. | |
| 5,879,385 A | 3/1999 | Crockard et al. | |
| 5,897,556 A | 4/1999 | Drewry et al. | |
| 5,954,504 A | 9/1999 | Misch et al. | |
| 5,989,290 A | 11/1999 | Biedermann et al. | |
| 6,010,502 A | 1/2000 | Bagby | |
| 6,143,032 A | 11/2000 | Schafer et al. | |
| 6,149,689 A | 11/2000 | Grundei et al. | |
| 6,206,924 B1 * | 3/2001 | Timm ................ | A61F 2/28 623/17.11 |
| 6,245,110 B1 | 6/2001 | Grundei et al. | |
| 6,264,695 B1 | 7/2001 | Stoy | |
| 6,280,478 B1 | 8/2001 | Richter et al. | |
| 6,290,726 B1 | 9/2001 | Pope et al. | |
| 6,379,385 B1 | 4/2002 | Kalas et al. | |
| 6,464,727 B1 | 10/2002 | Sharkey et al. | |
| 6,520,997 B1 * | 2/2003 | Pekkarinen ............ | A61F 2/00 623/23.72 |
| 6,585,770 B1 | 7/2003 | White et al. | |
| 6,660,041 B1 | 12/2003 | Grundei | |
| 6,712,852 B1 | 3/2004 | Chung et al. | |
| D493,533 S | 7/2004 | Blain | |
| 6,761,738 B1 | 7/2004 | Boyd | |
| 6,866,682 B1 | 3/2005 | An et al. | |
| 6,881,228 B2 | 4/2005 | Zdeblick et al. | |
| 6,931,812 B1 | 8/2005 | Lipscomb | |
| 6,972,019 B2 | 12/2005 | Michelson | |
| 7,156,874 B2 | 1/2007 | Paponneau et al. | |
| 7,163,560 B2 | 1/2007 | Mason | |
| 7,163,561 B2 | 1/2007 | Michelson | |
| 7,208,222 B2 * | 4/2007 | Rolfe ................ | A61B 17/8605 428/131 |
| 7,291,149 B1 | 11/2007 | Michelson | |
| 7,537,616 B1 | 5/2009 | Branch et al. | |
| 7,572,293 B2 | 8/2009 | Rhodes et al. | |
| 7,578,850 B2 | 8/2009 | Kuczynski et al. | |
| 7,621,950 B1 | 11/2009 | Globerman et al. | |
| 7,846,206 B2 * | 12/2010 | Oglaza ................ | A61F 2/442 623/17.11 |
| 8,062,365 B2 | 11/2011 | Schwab | |
| 8,292,967 B2 | 10/2012 | Brown et al. | |
| 8,906,074 B2 | 12/2014 | Kang | |
| 8,998,990 B2 | 4/2015 | Bertagnoli et al. | |
| 2004/0082999 A1 | 4/2004 | Mathys et al. | |
| 2004/0121451 A1 | 6/2004 | Mortiz et al. | |
| 2004/0236336 A1 | 11/2004 | Foerster | |
| 2005/0015154 A1 * | 1/2005 | Lindsey ................ | A61B 17/68 623/23.46 |
| 2005/0033425 A1 | 2/2005 | Schwab | |
| 2005/0129726 A1 | 6/2005 | Liebschner | |
| 2005/0143827 A1 | 6/2005 | Globerman et al. | |
| 2005/0171613 A1 | 8/2005 | Sartorius et al. | |
| 2005/0222683 A1 | 10/2005 | Berry | |
| 2006/0106461 A1 | 5/2006 | Embry et al. | |
| 2006/0147332 A1 | 7/2006 | Jones et al. | |
| 2006/0200062 A1 | 9/2006 | Saadat | |
| 2007/0027544 A1 | 2/2007 | McCord et al. | |
| 2007/0032876 A1 | 2/2007 | Clark | |
| 2007/0055376 A1 | 3/2007 | Michelson | |

(56) References Cited

U.S. PATENT DOCUMENTS

| | | | |
|---|---|---|---|
| 2007/0179610 | A1 | 8/2007 | Biedermann et al. |
| 2007/0233248 | A1 | 10/2007 | Schwab et al. |
| 2007/0255420 | A1 | 11/2007 | Johnson et al. |
| 2007/0270956 | A1 | 11/2007 | Heinz |
| 2008/0014457 | A1 | 1/2008 | Gennaro et al. |
| 2008/0071356 | A1 | 3/2008 | Greenhalgh et al. |
| 2008/0075752 | A1* | 3/2008 | Ratner .................... A61L 27/14 424/426 |
| 2008/0154314 | A1* | 6/2008 | McDevitt ........... A61B 17/8095 606/304 |
| 2009/0054987 | A1 | 2/2009 | Chin |
| 2009/0076508 | A1 | 3/2009 | Weinans et al. |
| 2009/0138015 | A1 | 5/2009 | Conner et al. |
| 2009/0149956 | A1* | 6/2009 | Greenhalgh ....... A61B 17/7061 623/17.11 |
| 2009/0222098 | A1 | 9/2009 | Trieu et al. |
| 2009/0228112 | A1 | 9/2009 | Clark et al. |
| 2009/0276048 | A1 | 11/2009 | Chirico et al. |
| 2010/0106194 | A1 | 4/2010 | Bonutti |
| 2010/0161061 | A1 | 6/2010 | Hunt |
| 2010/0174377 | A1 | 7/2010 | Heuer |
| 2010/0174380 | A1 | 7/2010 | Lewis |
| 2010/0179667 | A1 | 7/2010 | Day et al. |
| 2010/0228355 | A1 | 9/2010 | Linares |
| 2010/0298950 | A1 | 11/2010 | McDonnel et al. |
| 2011/0022180 | A1 | 1/2011 | Melkent et al. |
| 2011/0035020 | A1 | 2/2011 | Laughner et al. |
| 2011/0125284 | A1 | 5/2011 | Gabbrielli et al. |
| 2011/0196495 | A1 | 8/2011 | Hunt |
| 2011/0251690 | A1 | 10/2011 | Berger |
| 2011/0313532 | A1 | 12/2011 | Hunt |
| 2012/0290089 | A1 | 11/2012 | Melamed |
| 2013/0030529 | A1 | 1/2013 | Hunt |
| 2013/0030540 | A1 | 1/2013 | Leibinger |
| 2013/0123935 | A1 | 5/2013 | Hunt |
| 2013/0158672 | A1 | 6/2013 | Hunt |
| 2013/0218282 | A1 | 8/2013 | Hunt |
| 2014/0121776 | A1 | 5/2014 | Hunt |
| 2014/0288649 | A1 | 9/2014 | Hunt |
| 2014/0288650 | A1 | 9/2014 | Hunt |
| 2015/0282945 | A1 | 10/2015 | Hunt |
| 2015/0282946 | A1 | 10/2015 | Hunt |
| 2016/0287389 | A1 | 10/2016 | Hunt |
| 2016/0287404 | A1 | 10/2016 | Hunt |
| 2016/0287405 | A1 | 10/2016 | Hunt |
| 2017/0216035 | A1 | 8/2017 | Hunt |
| 2017/0319344 | A1 | 11/2017 | Hunt |
| 2017/0360563 | A1 | 12/2017 | Hunt |

FOREIGN PATENT DOCUMENTS

| | | |
|---|---|---|
| DE | 19721661 | 11/1998 |
| DE | 102006047663 | 4/2008 |
| EP | 0268115 | 1/1991 |
| EP | 0489684 | 6/1992 |
| WO | 0128460 | 4/2001 |
| WO | 2008022206 | 2/2008 |
| WO | 2010080511 | 7/2010 |

OTHER PUBLICATIONS

International Preliminary Report on Patentability for PCT/US2012/063600 dated May 6, 2014.
Supplemental European Search Report for EP Application No. 12846553.1 dated May 20, 2015.
Office Action for U.S. Appl. No. 13/762,825 dated Jul. 2, 2014.
Office Action for U.S. Appl. No. 13/762,825 dated Dec. 12, 2014.
International Search Report and Written Opinion for PCT/US2013/025281 dated May 15, 2013.
International Preliminary Report on Patentability for PCT/US2013/025281 dated Aug. 12, 2014.
Office Action for U.S. Appl. No. 14/036,974 dated Jul. 22, 2015.
International Search Report and Written Opinion for PCT/US2013/061725 dated Jan. 13, 2014.
International Preliminary Reporton Patentability for PCT/US2013/061725 dated Mar. 13, 2015.
International Search Report and Written Opinion for PCT/US2014/030319 dated Apr. 6, 2015.
Office Action for U.S. Appl. No. 14/216,087 dated Aug. 27, 2015.
"Rapid prototyping enables company to manufacture revolutionary new medical product", accessed at <http://www.newslettersonline.com/user/user.fas/s=63/fp=3/tp=47?T=open_article,565208&P=article>, Oct. 9, 2003. (pp. 1-2).
"Midiantic Medical Systems—Geo Structure Rectangles (Posterior Approach)" accessed Jun. 11, 2008 at <http://www.midlanticmedical.com/products/anteriorColumnSpacers.php?p=2>. (p. 1).
"Midiantic Medical Systems—Nexus (Transverse Approach)" accessed Jun. 11, 2008 at <http://www.midlanticmedical.com/products/anteriorColumnSpacers.php?p=4>. (p. 1).
"Zimmer® Trabecular Metal™ Technology", accessed at <http://www.zimmerindia.com/z/ctl/op/global/action/1/id/9512/template/PC/navid/8173>, Jul. 9, 2006. (pp. 1-5).
"Multifunctional Electrochemical Energy Storage Materials", accessed on Oct. 1, 2008 at <http://www.uvapf.org/technologies/index.cfm/fuseaction/invention/invention_id/85/?CFID=1785971&CFTOKEN=596497848> (pp. 1-2).
"Image: C60a.phg", Wikipedia, accessed on Oct. 1, 2008 at <http://en.wikipedia.org/wiki/Image:C60a.png>. (pp. 1-3).
"Image:POV-Ray-Dodecahedron.svg", Wikipedia, accessed at on Oct. 1, 2008 at <http://en.wikipedia.org/wiki/Image:POV-Ray-Dodecahedron.svg>. (pp. 1-4).
"Image:lcosahedron.svg", Wikipedia, accessed on Oct. 1, 2008 at <http://en.wikipedia.org/wiki/Image:lcosahedron.svg>. (pp. 1-2).
"Image:Octahedron.svg", Wikipedia, accessed on Oct. 1, 2008 at <http://en.wikipedia.org/wiki/Image:Octahedron.svg>. (pp. 1-3).
"Truss" Wikipedia, accessed at <http://en.wikipedia.org/wiki/Truss>, Dec. 16, 2009. (pp. 1-9).
"NexGen Trabecular Metal Tibial Cone Augments" accessed at <http://catalog.zimmer.com/content/zpc/products/200/250/C60/CE008/2653.html>, Nov. 17, 2009. (p. 1).
"Spinal Kinetics", accessed on Oct. 6, 2009 at <http://www.spinalkinetics.com/m6systems.html>. (p. 1).
"CINN", accessed on Oct. 6, 2009 at <http://www.cinn.org/cr-articles/CR-artificial-disc.html>, Copyright 2008. (pp. 1-9).
"Zimmer Anatomical Shoulder Fracture System", copyright 2007. (pp. 1-6).
"Wolffs Law", Wikipedia, accessed at <http://en.wikipedia.org/wiki/Wolffs_law>, Jun. 9, 2010. (pp. 1-2).
"e-Manufacturing is making its inroad to series production", Nov. 20, 2008. (pp. 1-2).
"InFix Anterior Lumbar Device" Dec. 17, 2009. (p. 1).
"Biofoam Wedge System" Wright, Copyright 2010. (pp. 1-4).
"LPT2 Great Toe Implant" Wright, Copyright 2008. (p. 1-16).
"Biofoam Wedge System Surgical Technique" Wright, Copyright 2010. (pp. 1-12).
Murr et al. "Next-generation biomedical implants using additive manufacturing of complex, cellular and functional mesh arrays", Philosophical Transactions of the Royal Society, Mar. 22, 2010, vol. 368, No. 1917, pp. 1999-2032.
Yan, et al. "Mechanical strain regulates osteoblast proliferation through integrin-mediated ERK activation", PloS One, Apr. 23, 2012, vol. 7, No. 4, Article No. e35709.
Distension Blog located at htpp://kineticdistensio.blogspot.com/2011_10_0_archive.html including entry of Oct. 14, 2011.
Baranovskaya et al. ITECH M. Sc. Programme-Uni Stuttgart, Institut Fur Computerbasiertes Entwerfen (ICD, Stuttgart, Germany located at htpp://architecture-is-yes.tumblr.com/post/8525760 accessed Aug. 21, 2015.
Office Action for U.S. Appl. No. 12/640,825 dated Aug. 30, 2012.
EPO International Search Report and Written Opinion for PCT/US2009/068512 dated May 12, 2010. (pp. 1-61).
International Preliminary Reporton Patentability for PCT/US2009/068512 dated Mar. 31, 2011. (pp. 1-8).
Office Action for U.S. Appl. No. 12/960,092 dated Aug. 20, 2014.
Office Action for U.S. Appl. No. 12/960,092 dated Apr. 24, 2015.

(56) References Cited

OTHER PUBLICATIONS

Australian Examination Report for Australian Patent Application No. 2009335771 dated Jan. 14, 2014.
European Examination Report for EP Application No. 09796208.8 dated Feb. 7, 2014.
European Examination Report for EP Application No. 09796208.8 dated Aug. 21, 2014.
Office Action for U.S. Appl. No. 12/818,508 dated Feb. 4, 2013.
Final Office Action for U.S. Appl. No. 12/818,508 dated Aug. 15, 2013.
Office Action for U.S. Appl. No. 12/818,508 dated May 22, 2015.
EPO International Search Report and Written Opinion for PCT/US2011/040117 dated Aug. 12, 2011.
International Preliminary Reporton Patentability for PCT/US2011/040117 dated Dec. 19, 2012.
Office Action for U.S. Appl. No. 13/805,231 dated Aug. 20, 2015.
Australian Examination Report for AU Application No. 2011267941 dated Jan. 16, 2014.
Japanese Examination Report for JP Application No. 2013-515407 dated Feb. 24, 2015.
Office Action for U.S. Appl. No. 13/194,561 dated Mar. 19, 2013.
Final Office Action for U.S. Appl. No. 13/194,561 dated Sep. 26, 2013.
Office Action for U.S. Appl. No. 13/194,561 dated Jan. 20, 2015.
International Search Report and Written Opinion for PCT/US2012/048300 dated May 7, 2013.
International Preliminary Report on Patentability for PCT/US2012/048300 dated Feb. 4, 2014.
International Search Report and Written Opinion for PCT/US2012/045717 dated Jan. 30, 2013.
International Preliminary Report on Patentability for POT/US2012/045717 dated Jan. 7, 2014.
Office Action for U.S. Appl. No. 13/668,968 dated Aug. 18, 2014.
Office Action for U.S. Appl. No. 13/668,968 dated Jan. 7, 2015.
Office Action for U.S. Appl. No. 13/668,968 dated Jun. 29, 2015.
Canadian Examination Report for Canadian Patent Application No. 2,746,505 dated Dec. 1, 2015.
Office Action for U.S. Appl. No. 14/743,579 dated Apr. 5, 2016.
Office Action for U.S. Appl. No. 14/743,607 dated Apr. 6, 2016.
Final Office Action for U.S. Appl. No. 12/818,508 dated Nov. 20, 2015.
Final Office Action for U.S. Appl. No. 13/805,231 dated Dec. 11, 2015.
Japanese Examination Report for JP Application No. 2013-515407 dated Nov. 24, 2015.
Japanese Examination Report for JP Application No. 2014-523976 dated May 24, 2016.
Office Action for U.S. Appl. No. 13/668,968 dated Apr. 14, 2016.
Office Action for U.S. Appl. No. 13/762,825 dated Mar. 7, 2016.
Chinese Examination Report for CN Application No. 201300555973 dated Apr. 5, 2016.
Cobos et al. "The Cylindrical Titanium Mesh Cage for Treatment of a Long Bone Segmental Defect Description of a New Technique and Report of Two Cases" Journal of Orthopaedic Trauma (2000) vol. 14, No. 1, pp. 54-59.
Lindsey et al. "The Efficacy of Cylindrical Titanium Mesh Cage for the Reconstruction of a Critical-Size Canine Segmental Remoral Diaphyseal Defect" Journal of Orthopaedic Research (Jul. 2006), pp. 1438-1453.
Office Action for U.S. Appl. No. 14/743,555 dated Sep. 27, 2016.
Final Office Action for U.S. Appl. No. 14/743,555 dated Jul. 3, 2017.
Australian Examination Report for Australian Patent Application No. 2013323602 dated Jul. 4, 2017.
Office Action for U.S. Appl. No. 12/818,508 dated Dec. 2, 2016.
Office Action for U.S. Appl. No. 13/805,231 dated Oct. 12, 2016.
Final Office Action for U.S. Appl. No. 13/805,231 dated Apr. 25, 2017.
Office Action for U.S. Appl. No. 13/805,231 dated Dec. 18, 2017.
Canadian Examination Report for Canadian Patent Application No. 2,803,015 dated Jun. 15, 2017.
European Examination Report for EP Application No. 11726306.1 dated Nov. 13, 2017.
Final Office Action for U.S. Appl. No. 13/668,968 dated Nov. 16, 2016.
Australian Examination Report for AU Application No. 2012332092 dated Feb. 14, 2017.
Australian Examination Report for AU Application No. 2012332092 dated Dec. 19, 2017.
Japanese Examination Report for JP Application No. 2014-540188 dated Jul. 14, 2016.
Office Action for U.S. Appl. No. 13/762,825 dated Sep. 20, 2016.
Australian Examination Report for AU Application No. 2013216947 dated Mar. 27, 2017.
European Examination Report for EP Application No. 13746753.6 dated Sep. 23, 2015.
European Examination Report for EP Application No. 13746753.6 dated Oct. 28, 2016.
Japanese Examination Report for JP Application No. 2014-556705 dated Nov. 29, 2016.
Japanese Examination Report for JP Application No. 2014-556705 dated Sep. 19, 2017.
Chinese Examination Report for CN Application No. 201300555973 dated Nov. 16, 2016.
Chinese Examination Report for CN Application No. 201300555973 dated Jun. 8, 2017.
Japanese Examination Report for JP Application No. 2013-533302 dated Aug. 15, 2017.
Australian Examination Report for AU Application No. 2013323602 dated Jul. 4, 2017.
Office Action for U.S. Appl. No. 14/215,961 dated Mar. 11, 2016.
Office Action for U.S. Appl. No. 14/216,087 dated Feb. 2, 2017.
International Search Report and Written Opinion for PCTUS201430358 dated Aug. 27, 2014.
Chinese Examination Report for CN Application No. 201480026652.0 dated Dec. 2, 2016.
European Examination Report for EP Application No. 14762747 dated Jan. 26, 2017.

* cited by examiner

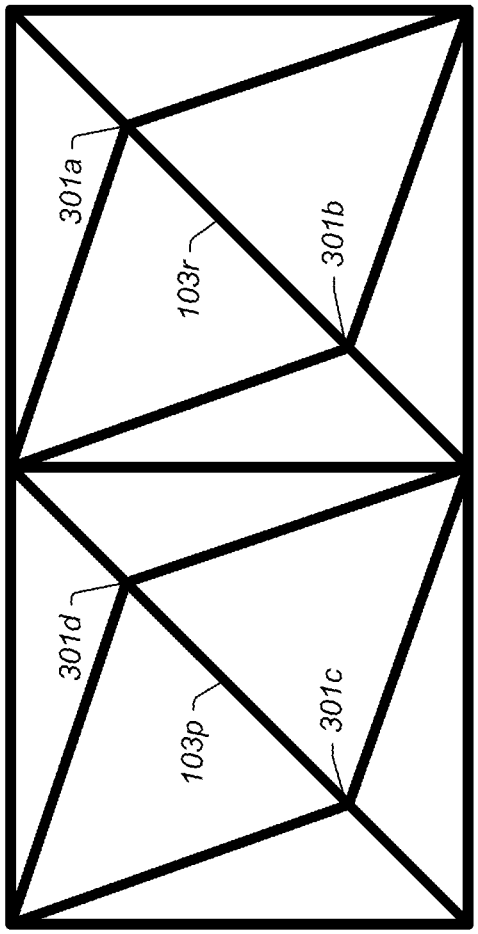
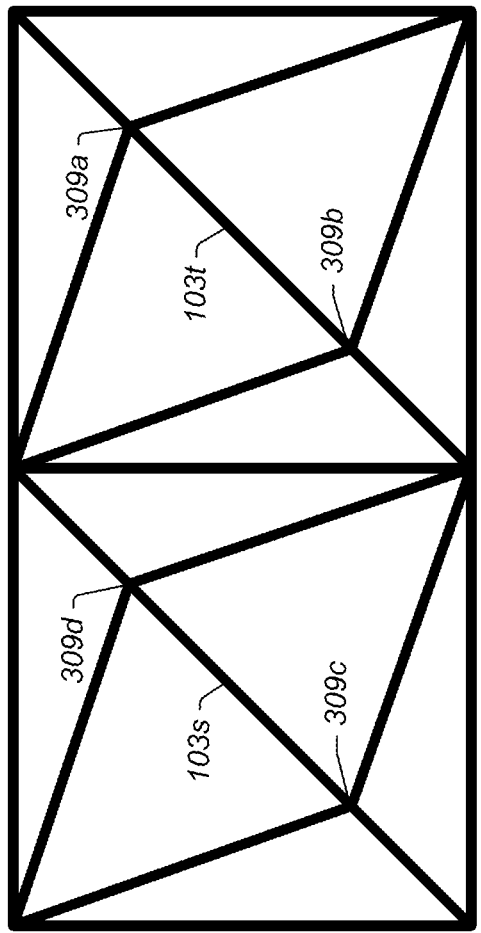

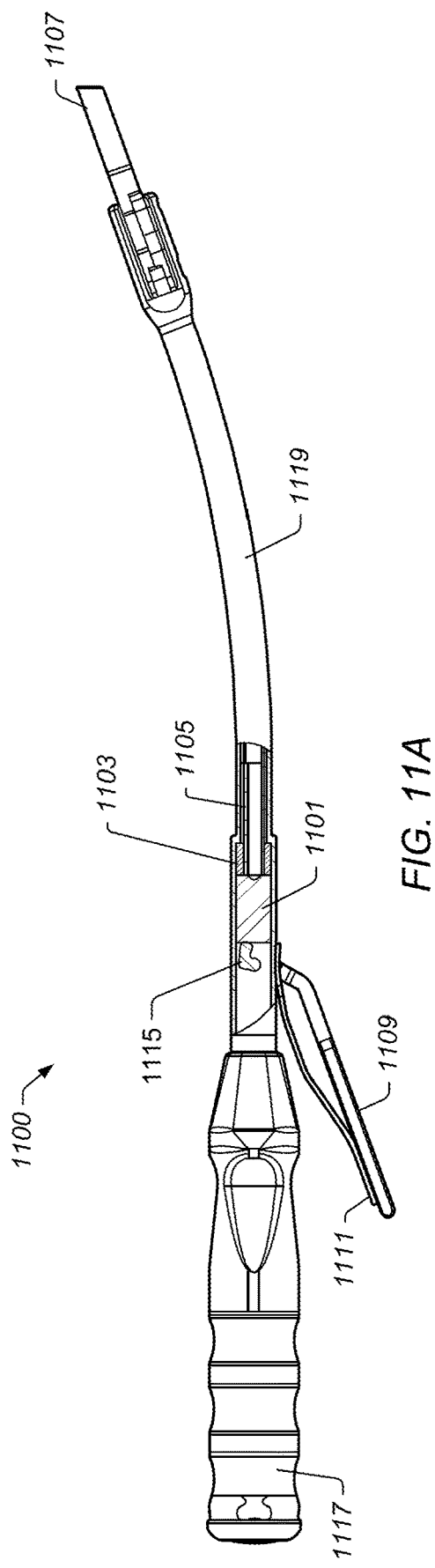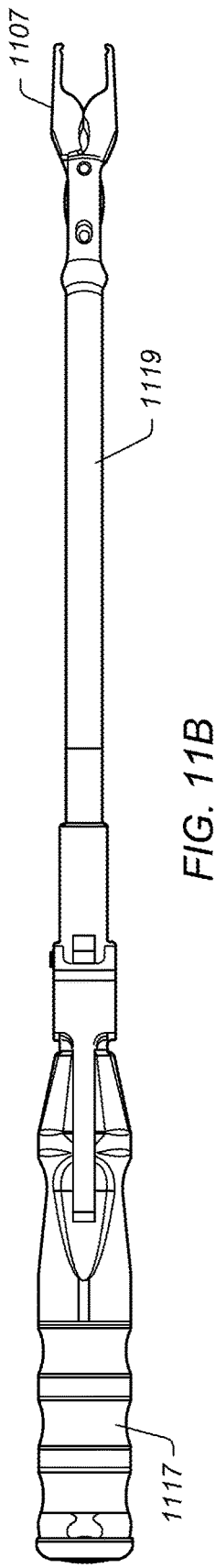
FIG. 11A
FIG. 11B

*Jaws Closed*

*Jaws Open*

IMPLANT DEVICE HAVING CURVED OR ARCED STRUTS

PRIORITY

This application is a continuation of U.S. patent application Ser. No. 12/960,092 entitled "Implant System and Method," filed Dec. 3, 2010 which is a continuation of U.S. patent application Ser. No. 12/640,825, entitled "Truss Implant", filed Dec. 17, 2009, which claims priority to U.S. Provisional Patent Application Ser. No. 61/138,707, entitled "Truss Implant", filed Dec. 18, 2008, all of which are hereby incorporated by reference in their entirety as though fully and completely set forth herein.

BACKGROUND

1. Field of the Invention

The present invention relates generally to medical devices and, more specifically, to implants.

2. Description of the Related Art

Implants may be used in human and/or animals to support and/or secure one or more bones. For example, implants may be used in the spine to support and/or replace damaged tissue between the vertebrae in the spine. Once implanted between two vertebrae, the implant may provide support between the two vertebrae and bone growth may take place around and through the implant to at least partially fuse the two vertebrae for long-term support. Implants may include relatively large rims with solid material that may cover, for example, 50% of the area that interacts with the endplate. The rim may provide a contact area between the implant and the vertebral endplates. Large rims may have several drawbacks. For example, large rims may impede bone growth and reduce the size of the bone column fusing the superior and inferior vertebral bodies.

Spinal implants may include open channels through the center of the supporting rims in a superior/inferior direction. The open channel design may require members of the implant that separate the rims that interact with the vertebral endplates to absorb the compressive forces between the vertebral endplates. This may increase the pressure on smaller areas of the vertebral endplates and may potentially lead to stress risers in the vertebral endplates. Further, while bone graft material is often used in conjunction with implants to encourage bone growth, the open column design of implants may reduce the likelihood of bone graft material from securing itself to the implant which could result in a bio-mechanical cooperation that is not conducive to promoting good fusion.

Bone graft material may be packed into the implant in a high-pressure state to prevent bone graft material from exiting the implant while being placed between the vertebral endplates. The high-pressure state may also reduce the potential for the bone graft material loosening due to motion between the implant and the vertebral endplates or compressive forces experienced during settling of the implant. In addition, a high-pressure environment may allow the bone graft material to re-model and fuse at greater strength. High-pressure states, however, may be difficult to create and maintain for the bone graft material in an implant.

SUMMARY

Various embodiments of implant systems and related apparatus, and methods of operating the same are described herein. In various embodiments, provided is an implant for interfacing with a bone structure includes a web structure, including a space truss, configured to interface with human bone tissue. The space truss includes two or more planar truss units having a plurality of struts joined at nodes.

In certain embodiments, an implant includes a web structure configured to interface with human bone tissue. The implant includes a space truss and an external truss. The space truss includes two or more planar truss units having a plurality of struts joined at nodes. The external truss includes one or more planar trusses having two or more adjacent planar truss units that lie in substantially the same plane.

In some embodiments, the planar truss units include a planar triangular truss unit having three substantially straight struts and three nodes in a triangular configuration. The space truss may include a plurality of planar truss units coupled to one another, wherein each of the truss units lies in a plane that is not substantially parallel to a plane of an adjacent truss unit that shares at least one strut.

In some embodiments, at least one strut passes through the central portion of the implant. At least one strut may connect two or more opposing vertices of the square shaped common truss unit. At least one strut may connect two opposed vertices of the octahedron.

In some embodiments, the implant includes an external truss structure. The external truss structure includes one or more planar trusses comprising two or more planar truss units disposed proximate an exterior of the space truss. The external truss structure includes at least one of a top, a bottom, or a side portion of the web structure.

The implant may include top and bottom faces wherein at least a portion of the top and bottom faces are angled relative to one another to provide lordosis. The lordosis may be configured to be greater than approximately four degrees. The implant further includes a top external truss structure portion and a bottom external truss structure portion angled relative to one another such that a thickness of an anterior or a posterior region of the implant is greater than a thickness of the other of the anterior or the posterior region of the implant.

The web structure is configured to provide support along at least four planes of the implant to bear against tensile, compressive, and shear forces acting on the implant.

In some embodiments, the space truss comprises truss units forming a plurality of tetrahedrons. At least two of the plurality of tetrahedrons are coupled together via one or more struts connecting two respective vertices on each of the two tetrahedrons. The space truss may include a plurality of tetrahedrons, and wherein at least two of the tetrahedrons share a common truss unit to form a hexahedron. The space truss may include at least five truss units forming a pyramid. At least two of the pyramids are arranged opposing one another such that they share a square shaped common truss unit at their base to form an octahedron.

The implant may be configured for use as a spinal implant, a corpectomy device, in a hip replacement, in a knee replacement, in a long bone reconstruction scaffold, foot and ankle implant, shoulder implant, a joint replacement or in a cranio-maxifacial implant.

In some embodiments, the plurality of struts of the web structure have a diameter less than approximately five millimeters. In some embodiments, the struts that create the space truss comprises a biologic, growth factor or antimicrobial coupled thereto.

The implant may include an implant body comprising one or more contact faces configured to be disposed at or near a bony structure during use, wherein the web structure is disposed on the contact surface, and wherein the web structure includes two or more struts extending from the contact surface, and wherein two or more of the struts define an opening configured to enable bone through growth through the opening.

In some embodiments, a method is provided that includes accessing an intersomatic space and inserting an implant into the intersomatic space. The implant includes a web structure that includes a space truss to interface with human bone tissue. The space truss includes two or more planar truss units having a plurality of struts joined at nodes.

In certain embodiments, a method of making an implant includes storing a three-dimensional model of the implant on a storage medium, applying a layer of material to a support, moving an electron beam relative to the support to melt a portion of the material, wherein the electron beam is moved in a pattern determined from the three-dimensional model of at least a portion of the implant, and removing the implant from the support. The implant includes a web structure that includes a space truss to interface with human bone tissue. The space truss includes two or more planar truss units having a plurality of struts joined at nodes.

In some embodiments, provided is an implant that includes an implant body having one or more contact faces to be disposed at or near a bony structure, and a truss structure coupled to the contact face. The truss structure is to be disposed adjacent the bony structure during use, and includes two or more struts extending from the contact surface, wherein two or more of the struts define an opening to enable bone through growth through the opening.

In certain embodiments, provided is a method that includes slitting at least a portion of a bony structure to form one or more slits extending from a face of the bony structure into the bony structure, and inserting at least a portion of a truss structure of an implant into at least one of the slits. The implant includes an implant body having one or more contact faces to be disposed at or near the bony structure and the truss structure coupled to the contact face. The truss structure is to be disposed adjacent the bony structure during use, and the truss structure includes two or more struts extending from the contact surface, wherein two or more of the struts define an opening to enable bone through growth through the opening.

BRIEF DESCRIPTION OF THE DRAWINGS

A better understanding of the present invention may be obtained when the following detailed description is considered in conjunction with the following drawings, in which:

FIGS. 4A-4B illustrate a top structure of an internal web structure of the implant, according to an embodiment.

FIGS. 11A-11D illustrate various views of an implant handler, according to an embodiment.

Figure 1A:
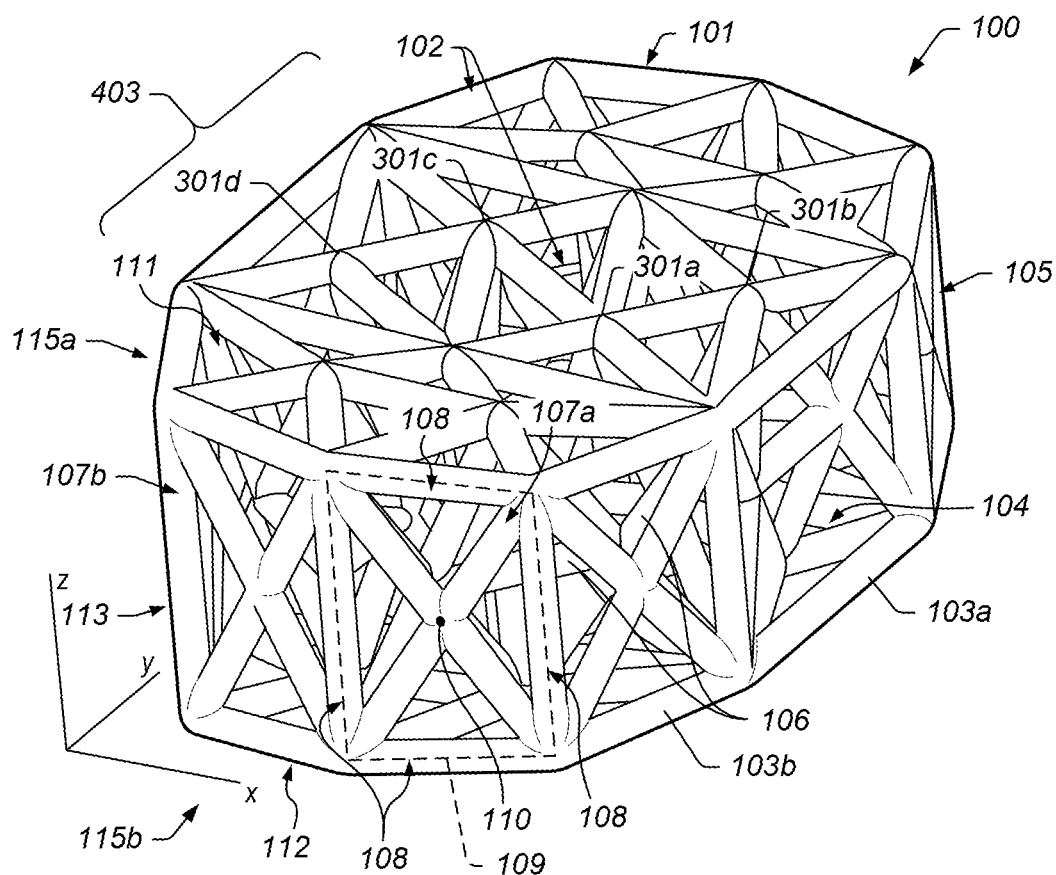
FIGS. 1A-1B illustrate views of an implant with lordosis, according to an embodiment.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents, and alternatives falling within the spirit and scope of the present invention as defined by the appended claims. Note, the headings are for organizational purposes only and are not meant to be used to limit or interpret the description or claims.

DETAILED DESCRIPTION OF THE EMBODIMENTS

Figure 1B:
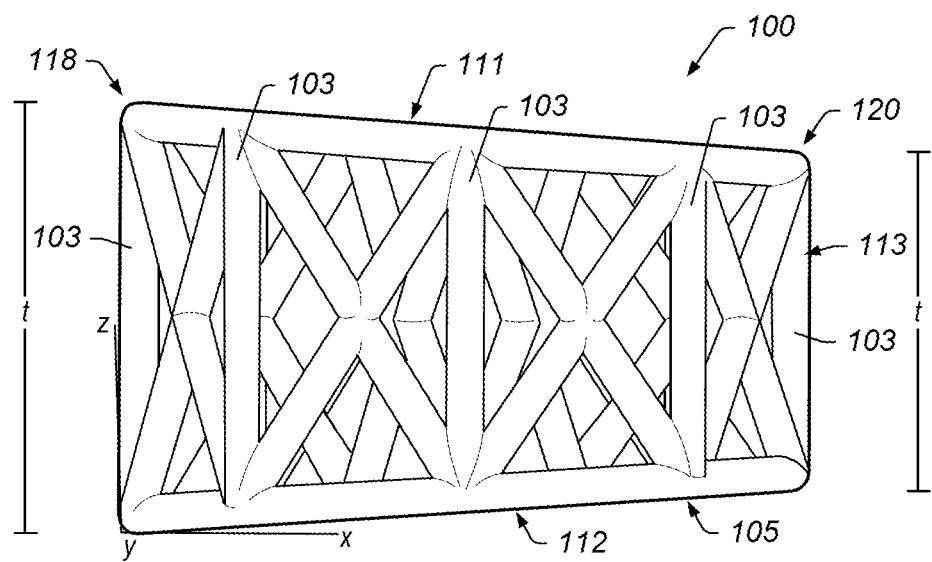

FIGS. 1A-1B illustrate views of implant 100, according to an embodiment. Implant 100 may be used, for example, in anterior lumbar inter-body fusion (ALIF) or posterior lumbar inter-body fusion (PLIF). In some embodiments, implant 100 may include a web structure 101 with one or more trusses 102 (e.g., planar and space trusses). Implant 100 and its web structure 101 may be used in various types of implants for humans or animals such as spinal implants (e.g., see FIGS. 1A-2D and 5A-6D)), corpectomy devices (e.g., see FIGS. 2C-2D), knee replacements (e.g., see FIG. 14), hip replacements (e.g., see FIG. 15), long bone reconstruction scaffolding (e.g., see FIG. 16), and cranio-maxifacial implants (e.g., see FIG. 17). Other implant uses are also contemplated.

As used herein a "truss" is a structure having one or more elongate struts connected at joints referred to as nodes. Trusses may include variants of a pratt truss, king post truss, queen post truss, town's lattice truss, planar truss, space truss, and/or a vierendeel truss (other trusses may also be used). Each unit (e.g., region having a perimeter defined by the elongate struts) may be referred to as a "truss unit."

As used herein a "planar truss" is a truss structure where all of the struts and nodes lie substantially within a single two-dimensional plane. A planar truss, for example, may include one or more "truss units" where each of the struts is a substantially straight member such that the entirety of the struts and the nodes of the one or more truss units lie in substantially the same plane. A truss unit where each of the struts is a substantially straight member such that the entirety of the struts and the nodes of the truss units lie in substantially the same plane is referred to as a "planar truss unit."

As used herein a "space truss" is a truss having struts and nodes that are not substantially confined in a single two-dimensional plane. A space truss may include two or more planar trusses (e.g., planar truss units) wherein at least one of the two or more planar trusses lies in a plane that is not substantially parallel to a plane of at least one or more of the other two or more planar trusses. A space truss, for example, may include two planar truss units adjacent to one another (e.g., sharing a common strut) wherein each of the planar truss units lie in separate planes that are angled with respect to one another (e.g., not parallel to one another).

As used herein a "triangular truss" is a structure having one or more triangular units that are formed by three straight struts connected at joints referred to as nodes. For example, a triangular truss may include three straight elongate strut members that are coupled to one another at three nodes to from a triangular shaped truss. As used herein a "planar triangular truss" is a triangular truss structure where all of the struts and nodes lie substantially within a single two-dimensional plane. Each triangular unit may be referred to as a "triangular truss unit." A triangular truss unit where each of the struts is a substantially straight member such that the entirety of the struts and the nodes of the triangular truss units lie in substantially the same plane is referred to as a "planar triangular truss unit." As used herein a "triangular space truss" is a space truss including one or more triangular truss units.

In various embodiments, the trusses 102 of web structure 101 may include one or more planar truss units (e.g., planar triangular truss units) constructed with straight or curved/arched members (e.g., struts) connected at various nodes. In some embodiments, the trusses 102 may be micro-trusses. A "micro-truss" may include a truss having dimensions sufficiently small enough such that a plurality of micro-trusses can be assembled or other wise coupled to one another to form a web structure having a small enough overall dimension (e.g., height, length and width) such that substantially all of the web structure can be inserted into an implant location (e.g., between two vertebra). Such a web structure and its micro-trusses can thus be employed to receive and distribute throughout the web structure loading forces of the surrounding tissue (e.g., vertebra, bone, or the like). In one embodiment, the diameters of the struts forming the micro-truss may be between about 0.25 millimeters (mm) and 5 mm in diameter (e.g., a diameter of about 0.25 mm, 0.5 mm, 0.6 mm, 0.7 mm, 0.8 mm, 0.9 mm, 1 mm, 2 mm, 3 mm, 4 mm, or 5 mm). In one embodiment, a micro-truss may have an overall length or width of less than about 1 inch (e.g., a length less than about 0.9 in, 0.8 in, 0.7 in, 0.6 in, 0.5 in, 0.4 in, 0.3 in, 0.2 in, 0.1 in).

As depicted, for example, in FIGS. 1A-1B, web structure 101 may extend throughout implant 100 (including the central portion of implant 100) to provide support throughout implant 100. Trusses 102 of implant 100 may thus support implant 100 against tensile, compressive, and shear forces. The web structure of trusses 102 may also reinforce implant 100 along multiple planes. The external truss structure may, for example, provide support against tensile and compressive forces acting vertically through the implant, and the internal web structure may provide support against tensile, compressive, and shear forces along the various planes containing the respective trusses. In some embodiments, the web structure includes trusses 102 that form a triangulated web structure with multiple struts (e.g., struts 103a-f) (struts are generally referred to herein as "struts 103").

In one embodiment, web structure 101 of the implant 100 may include an internal web structure that is at least partially enclosed by an external truss structure. For example, in one embodiment, web structure 101 may include an internal web structure that includes a space truss having at least a portion of the space truss surrounded by an external truss structure that includes one or more planar trusses formed with a plurality of planar truss units that lie substantially in a single plane. FIG. 1A depicts an embodiment of implant 100 and web structure 101 that includes internal web structure 104 and an external truss structure 105. In the illustrated embodiment, internal web structure 104 includes a space truss defined by a plurality of planar truss units 106 coupled at an angle with respect to one another such that each adjacent truss unit is not co-planar with each adjacent truss units. Adjacent truss units may include two truss units that share a strut and the respective two nodes at the ends of the shared strut.

In one embodiment, external truss structure 105 includes a plurality of planar trusses that are coupled about an exterior, interior or other portion of the implant. For example, in the illustrated embodiment, the external truss structure 105 includes a series of planar trusses 107a,b that are coupled to one another. Each planar truss 107a,b includes a plurality of planar truss units 108 that are coupled to one another and lie substantially in the same plane. As depicted, planar truss 107a includes four triangular planar truss units 108 having a common vertex 110 and arranged to form a generally rectangular structure that lies in a single common plane 109. In other words, the four truss units are arranged to form a substantially rectangular structure having "X" shaped struts extend from one corner of the rectangular structure to the opposite corner of the rectangular structure. As depicted, the substantially rectangular structure may include a trapezoidal shape. As described in more detail below, the trapezoidal shape may be conducive to providing an implant including lordosis. Lordosis may include an angled orientation of surfaces (e.g., top and bottom) of an implant that provides for differences in thickness in anterior and posterior regions of the implant such that the implant is conducive for supporting the curvature of a vertebral column.

In one embodiment, the planar trusses that form the external truss are coupled to one another, and are aligned along at least one axis. For example, in FIG. 1A, planar truss section 107a is coupled to an adjacent planar truss 107b. Planer truss sections 107a,b are not parallel in all directions. Planar truss sections 107a,b are, however, arranged parallel to one another in at least one direction (e.g., the vertical direction between the top and the bottom faces of implant 100). For example, planar trusses 107a,b and the additional planar trusses are arranged in series with an angle relative to one another to form a generally circular or polygon shaped enclosure having substantially vertical walls defined by the planar trusses and the planar truss units arranged in the vertical direction.

Figure 2A:
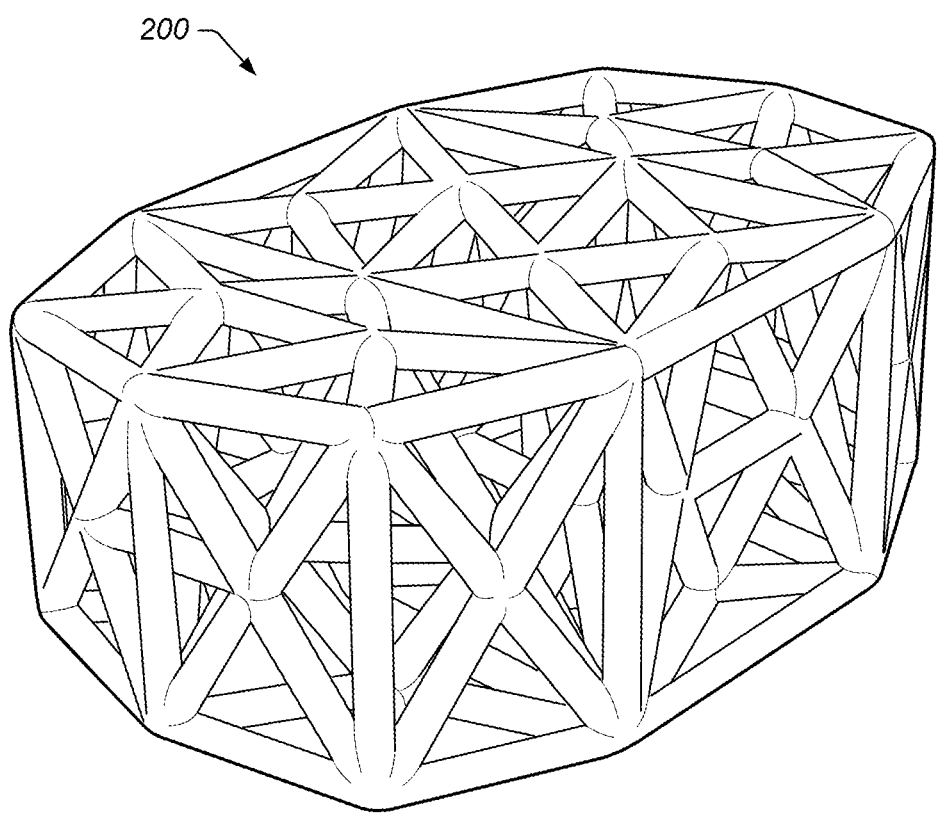
FIGS. 2A-2D illustrate views of an implant without lordosis, according to an embodiment.
Figure 2B:
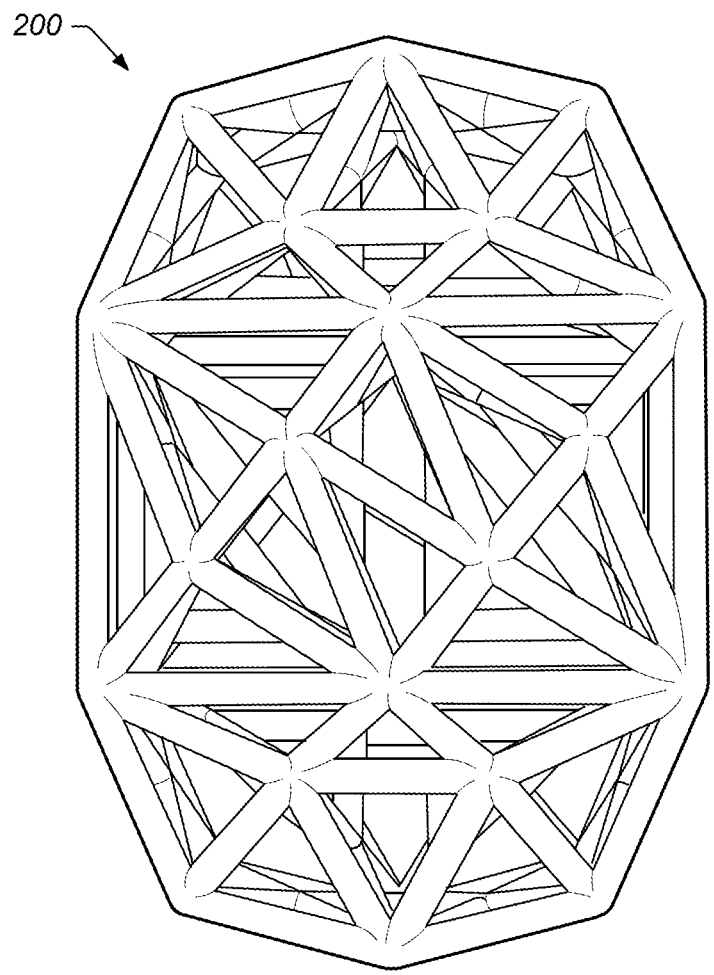
Figure 2C:
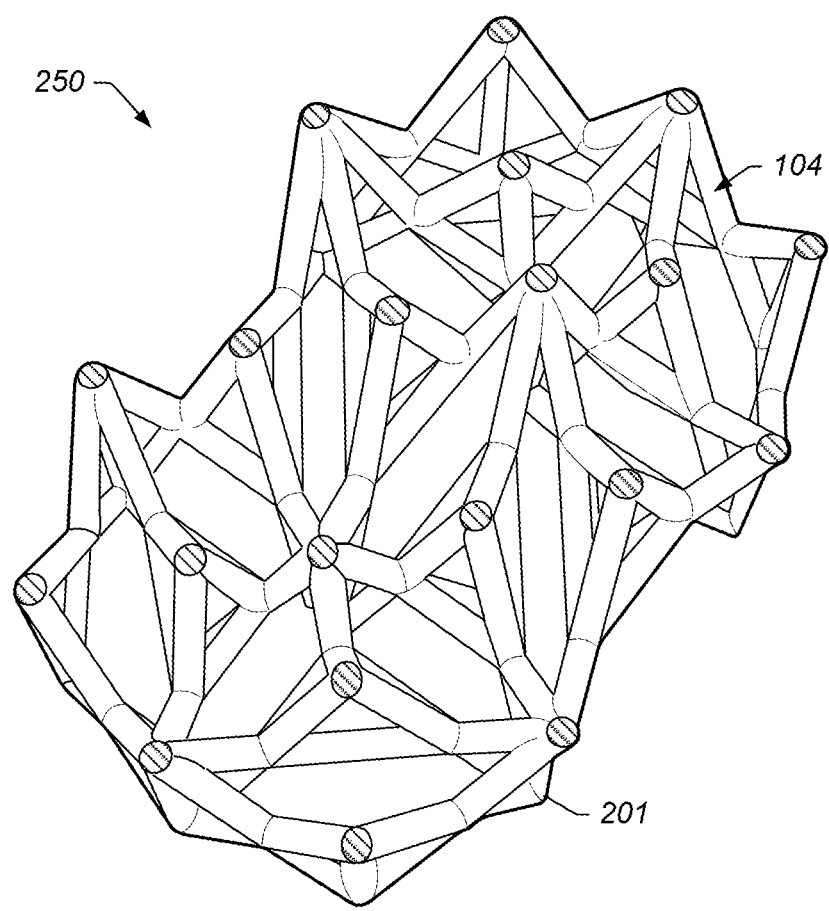

In one embodiment, the external truss portion may encompass the sides, top, and/or bottom of the implant. For example, in one embodiment, the external truss portion may include a top region, side regions, and/or a bottom region. FIG. 1A depicts an embodiment of implant 100 wherein external truss portion 105 includes a top 111, bottom 112 and a side region 113. As described above, side region 113 includes a series of planar trusses arranged vertically to form a circular/polygon ring-like structure that completely or at least partially surrounds the perimeter of the space truss disposed in the central portion of implant 100. In the depicted embodiment, top portion 111 of external truss structure 105 includes a plurality of truss units coupled to one another to form a planar truss that cover substantially all of the top region of internal web structure 104. In the illustrated embodiment, the top portion 111 spans entirely the region between top edges of the side portion 113 of external truss structure 105. In the illustrated embodiment, top portion 111 is formed from a single planar truss that includes a plurality of truss units that lie in substantially the same plane. In other words, the planar truss of top portion 111 defines a generally flat surface. Although difficult to view in FIG. 1, the underside of implant 100 may include the bottom portion 112 having a configuration similar to that of the top portion 111. In other embodiments, external truss structure 105 may include a partial side, top and/or bottom external truss portions. Or may not include one or more of the side, top and bottom external truss portions. For example, as described in more detail below, FIG. 2C depicts an embodiment of implant 100 than includes an internal web structure 104 that includes a space truss, and does not have an external truss structure.

In some embodiments, implant 100 may include a biocompatible material such as a titanium alloy (e.g., γTitanium Aluminides), cobalt, chromium, stainless steel, Polyetheretherketone (PEEK), ceramics, etc. Other materials are also contemplated. In some embodiments, implant 100 may be made through a rapid prototyping process (e.g., electron beam melting (EBM) process) as further described below. Other processes are also possible (e.g., injection molding, casting, sintering, selective laser sintering (SLS), Direct Metal Laser Sintering (DMLS), etc). SLS may include laser-sintering of high-performance polymers such as that provided by EOS of North America, Inc., headquartered in Novi, Mich., U.S.A. High-performance polymers may include various forms of PEEK (e.g., HP3 having a tensile strength of up to about 95 mega Pascal (MPa) and a Young's modulus of up to about 4400 MPa and continuous operating temperature between about 180° C. (356° F.) and 260° C. (500° F.)). Other materials may include PA 12 and PA 11 provided by EOS of North America, Inc.

Figure 8A:
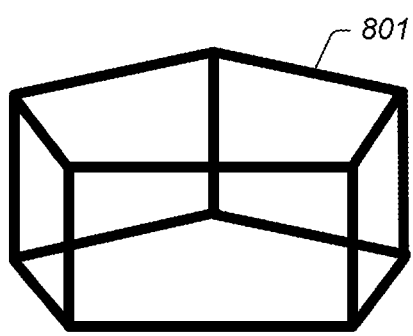
FIGS. 8A-8D illustrate different web structure building blocks, according to various embodiments.
Figure 8B:
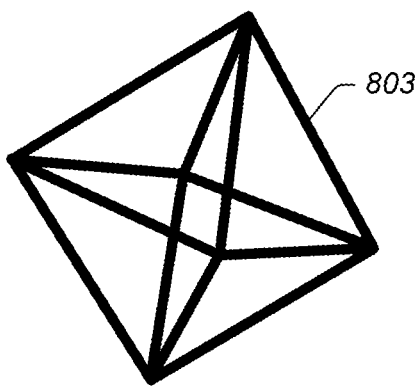
Figure 8C:
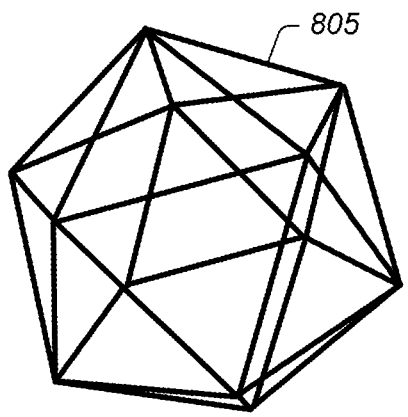
Figure 8D:
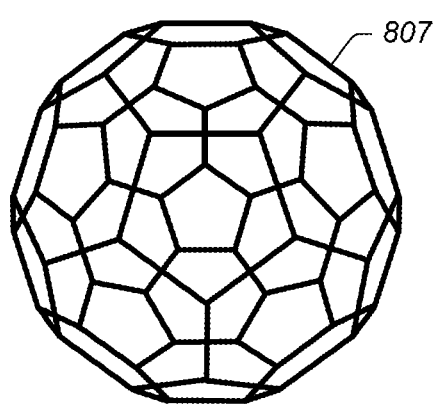
Figure 9:
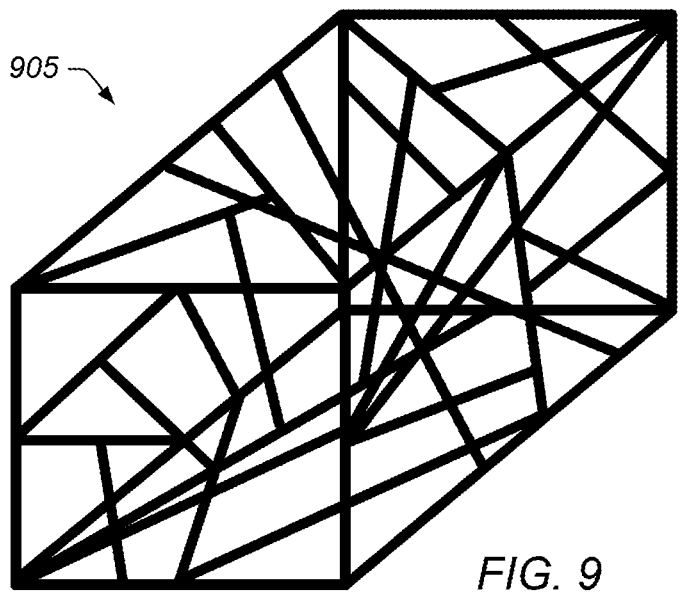
FIG. 9 illustrates a random web structure, according to an embodiment.

As described above, in some embodiments the trusses may form a triangulated web structure with multiple struts 103. The web structure may include a pattern of geometrical building blocks. In some embodiments, the geometrical building blocks may include triangles. In some embodiments, the geometrical building blocks may include polyhedrons such as tetrahedrons (e.g., see tetrahedrons 300a,b in FIG. 3), pentahedrons, hexahedrons, heptahedrons (e.g., see heptahedron 801 in FIG. 8A) and pyramids (e.g., see pyramids 705a,b in FIG. 7A), heptahedrons 705a,b in FIG. 7B), octahedrons (e.g., see octahedron 803 in FIG. 8B), dodecahedrons (e.g., see dodecahedrons 700a,b in FIG. 7C), and icosahedrons (e.g., see icosahedron 805 in FIG. 8C). Other geometrical building blocks are also contemplated (e.g., spherical fullerenes 807 in FIG. 8D). In some embodiments, such as those described above, the space truss of the web structure may connect multiple midpoints of tetrahedron building blocks and include a regular pattern of tetrahedron blocks arranged adjacent one another. In some embodiments, the web structure may not include a pattern of geometrical building blocks. For example, FIG. 9 illustrates an irregular pattern of struts 103 that may be used in implant 100. Other web structures are also contemplated.

Figure 3A:
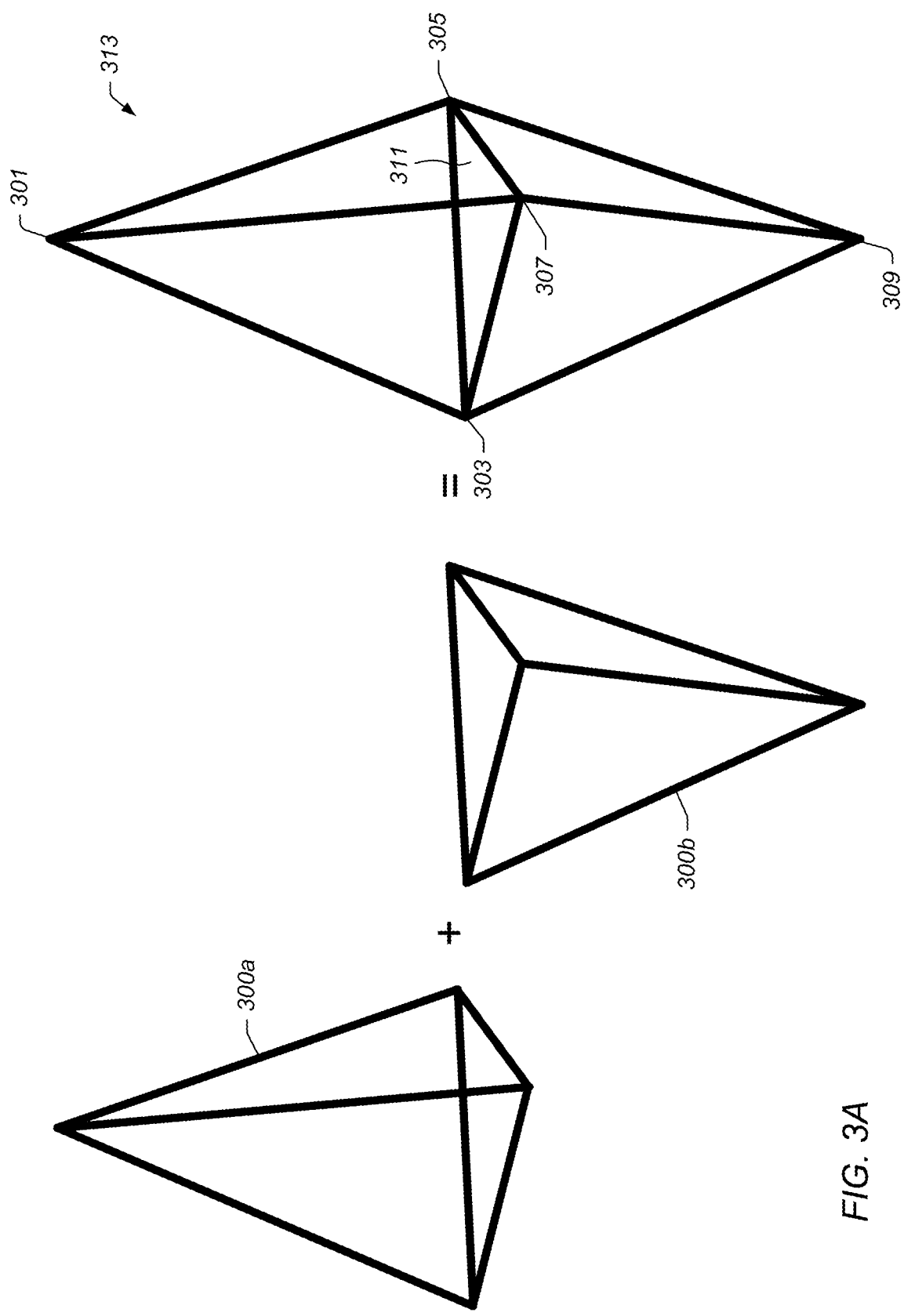
FIGS. 3A-3B illustrate a web structure formed with triangular-shaped building blocks, according to an embodiment.
Figure 3B:
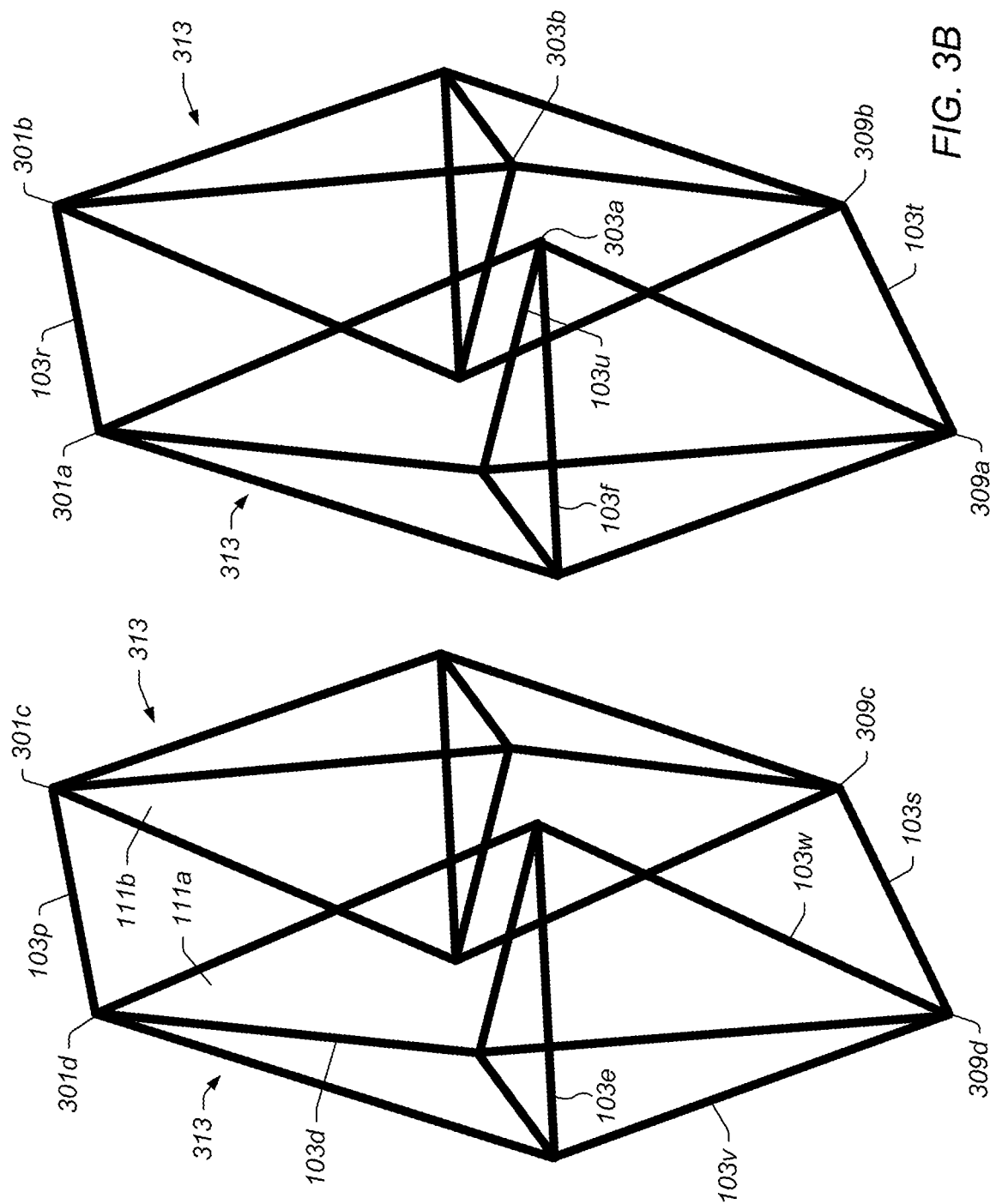

FIGS. 3A-3B illustrate a web structure formed with triangular-shaped building blocks, according to an embodiment. The triangular shaped building blocks may form tetrahedrons 300a,b that may also be used as building blocks (other patterns from the triangles are also contemplated). Other building blocks are also contemplated (e.g., square-shaped building blocks). In some embodiments, a web structure may include a single tetrahedron, such as tetrahedron 300a or 300b alone or in combination with one or more other web structures. In some embodiments, web structure 313 may include two or more tetrahedrons 300a,b. Tetrahedron 300a may include four triangular faces in which three of the four triangles meet at each vertex. In some embodiments, two tetrahedrons 300a and 300b may be placed together at two adjacent faces to form web structure 313 with a hexahedron-shaped frame (including six faces). Hexahedron-shaped web structure 313 may include first vertex 301, second vertex 309, third vertex 303, fourth vertex 305, and fifth vertex 307. Common plane 311 may be shared by two tetrahedrons (e.g., common plane 311 may include third vertex 303, fourth vertex 305, and fifth vertex 307) to form a hexahedron with first vertex 301 and second vertex 309 spaced away from common plane 311. As depicted, the center portion of the triangular shaped building blocks may have a void region in their center that does not include any additional members (e.g., no members other than the struts forming the triangular shaped building blocks) extending there through.

As seen in FIG. 3B, in some embodiments, multiple hexahedron-shaped web structures 313 may be arranged in a side-by-side manner Two web structures 313 of implant 100 may be connected via their first vertices 301a,b through strut 103r and connected via their second vertices 309a,b through strut 103t. Similarly, two web structures 313 may be connected via their first vertices 301c,d through strut 103p and connected via their second vertices 309c,d through strut 103s. Other connections are also possible. For example, web structures 313 may connect directly through side vertices (e.g., directly through corresponding vertices (such as vertices 303a,b) and/or share a common strut (such as strut 103u)) and/or through a side face (e.g., side faces 111a,b). Other struts are also shown (e.g., struts 103v, 103w).

FIG. 4A illustrates additional struts 103 (e.g., struts 103p and 103r) connecting the first vertices (represented respectively by 301a, 301b, 301c, and 301d) of four hexahedron-shaped web structures 313 in implant 100. FIG. 4B illustrates additional struts 103 (e.g., struts 103s and 103t) connecting second vertices 309 (represented respectively by 309a, 309b, 309c, and 309d) of four hexahedron-shaped web structures 313 in implant 100. In some embodiments, additional struts 103 may also be used internally between one or more vertices of the web structures to form additional trusses (e.g., see web structures in FIGS. 1A-2B) (other structures are also possible).

In some embodiments, top surface 115a and bottom surface 115b of implant 100 may include triangles, squares, circles or other shapes (e.g., a random or custom design). Top and bottom surfaces 115a,b may be used to connect the top and bottom vertices of various geometrical building blocks used in the web structure of implant 100. For example, each vertex may be connected through struts to the neighboring vertices of other geometrical building blocks. Top surface 115a may include other strut networks and/or connections. In some embodiments, bottom surface 115b may minor the top surface (and/or have other designs). In some embodiments, top surface 115a and bottom surface 115b may engage respective surfaces of two adjacent vertebrae when implant 100 is implanted.

As depicted in FIG. 1B, implant 100 may include lordosis (e.g., an angle in top and/or bottom surfaces 115a,b approximately in a range of 4 to 15 degrees (such as 4, 5, 6, 7, 8, 9, 10, 11, 12, 13, 14, or 15 degrees)) to further support the adjacent vertebrae when implanted. As described above, lordosis may include an angled orientation of surfaces (e.g., top and bottom) that provide for differences in thickness in the anterior and posterior portions of the implant such that the implant is conducive for supporting the curvature of a vertebral column. In the illustrated embodiment, the thickness of implant 100 is greater at or near the anterior portion 118 and lesser at or near the posterior portion 120 of the implant. In the illustrated embodiment, the side portions of external truss structure 105 are arranged substantially vertically, and the lordosis is formed by the angles of the top portion 111 and bottom portion 112 of external truss structure 105. For example, in the illustrated embodiment, top portion 111 and bottom portion 112 of external truss structure 105 are not perpendicular to the vertical plane defined by the side portion 113. Rather, the top portion 111 and bottom portion 112 are arranged with an acute angle relative to the vertical plane of side portion 113 at or near the anterior region 118 of implant 100 and with an obtuse angle relative to the vertical plane of side portion 113 at or near posterior region 120 of implant 100. As depicted, the vertical struts 103 that form the planar truss of side portion 113 of external truss structure 105 proximate posterior region 120 of implant 100 are shorter than struts 103 that form side portion 113 of external truss structure 105 proximate anterior region 118 of implant 100. In the illustrated embodiment, in which the vertical trusses 103 are substantially evenly spaced, the struts 103 forming the "X" cross members of the side planar trusses proximate the posterior region 120 of implant 100 are shorter than struts forming the "X" cross members of the side planar trusses proximate the anterior region 118 of implant 100. Other embodiments may include variations in the arrangement of the trusses to provide various configurations of the implant. For example, in some embodiments only one or neither of the top and bottom external truss portions may be non-perpendicular to the side portions of the external truss proximate the anterior and posterior portions of the implant. Further, the side, top, and/or bottom portions may include multiple planar trusses angled relative to one another in any orientation. For example, the top or bottom portions may include four planar trusses, each formed of multiple truss units, such that the portion(s) includes a pyramidal like shape.

Figure 2D:
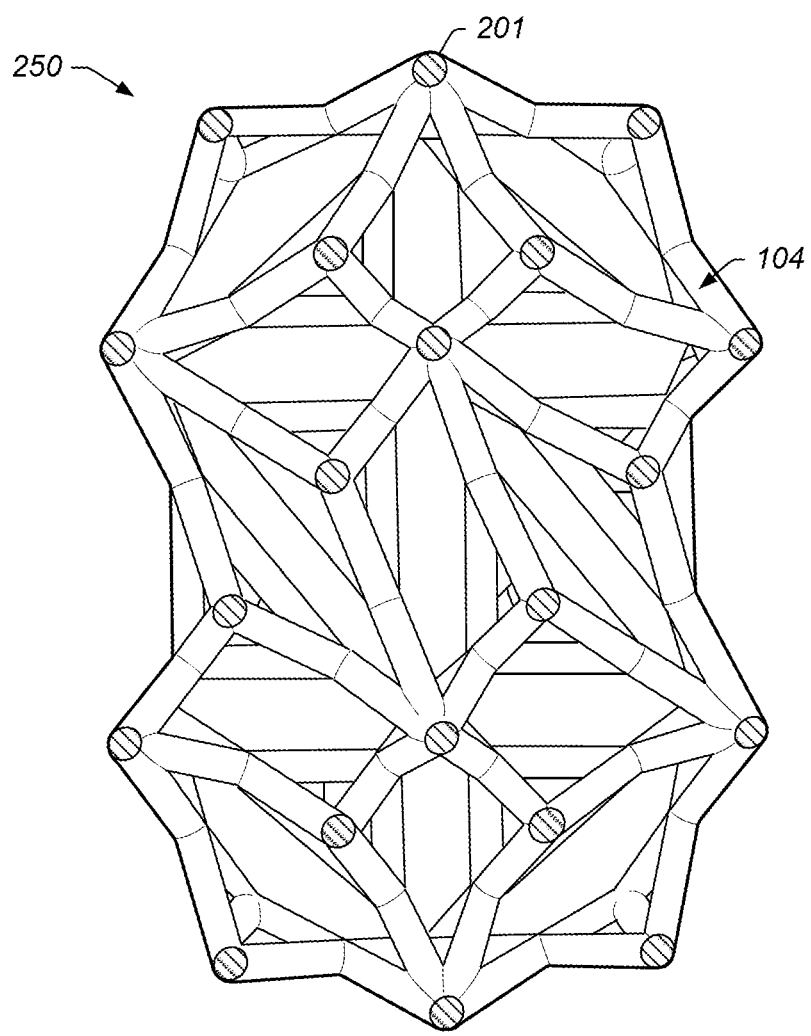

In some embodiments, the implant may not include lordosis. For example, FIGS. 2A-2B illustrate two views of an embodiment of an implant 200 without lordosis. In some embodiments, the top surface and bottom surface may not include connecting struts. For example, FIGS. 2C-2D illustrate two views of implant 250 without outer struts (e.g., without external truss portions formed of planar trusses). In the illustrated embodiment, implant 250 includes internal web structure 104 (e.g., a space truss) and does not include an external truss structure. For example, in the illustrated embodiment, the exterior faces of implant 250 are defined by a plurality of truss units that are angled relative to each of its adjacent truss units. The relative alignment of the truss units results in a non-planar exterior that includes a plurality of pointed junctions. The pointed junctions (e.g., pointed junction 201) may operate to dig into the surrounding bone to hold the implant in place (for example, if the implant is being used in a corpectomy device).

Figure 5A:
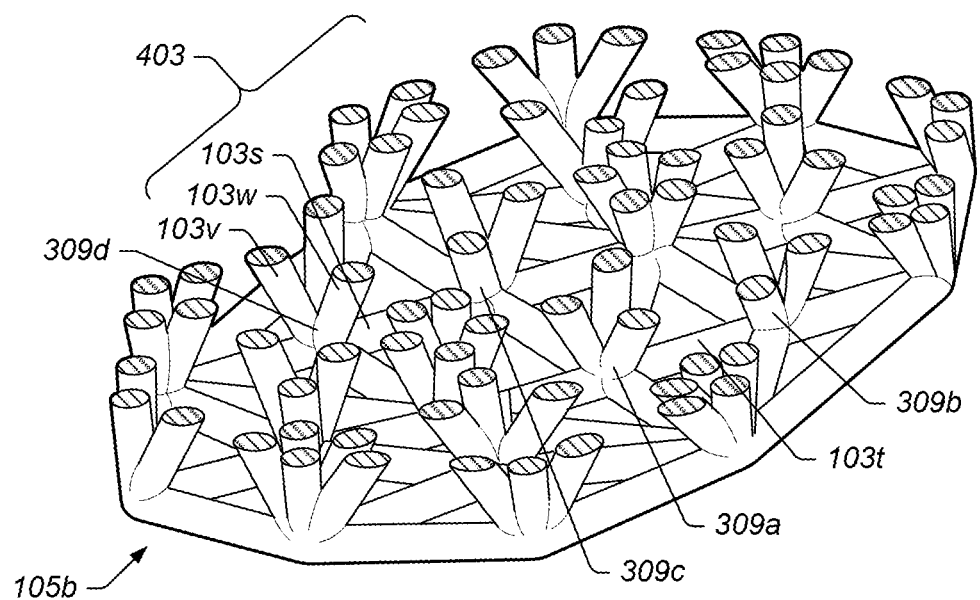
FIGS. 5A-5C illustrate progressive sectioned views of the implant showing the internal structure of the implant, according to an embodiment.
Figure 5B:
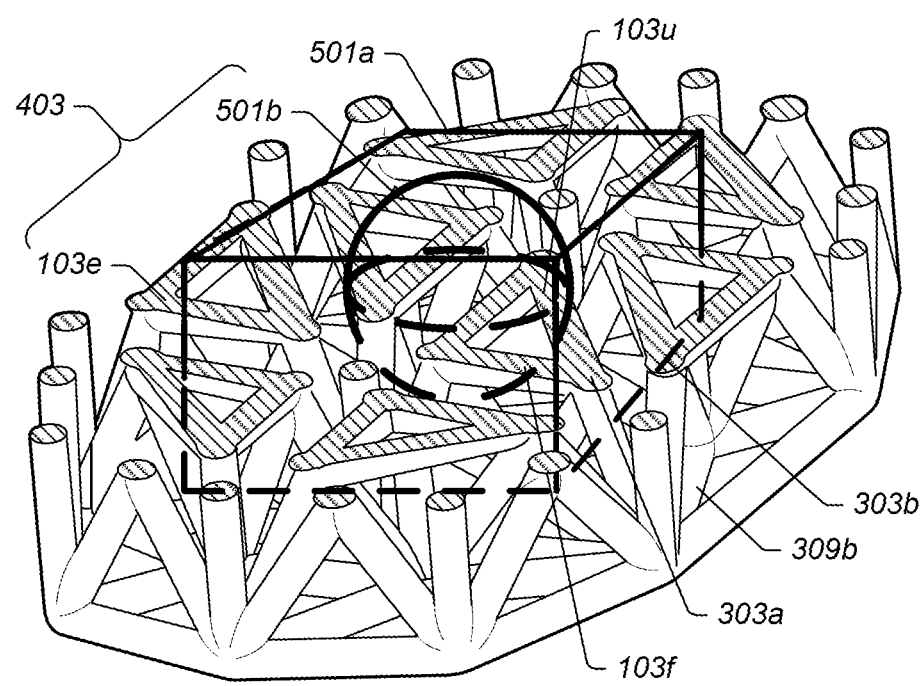
Figure 5C:
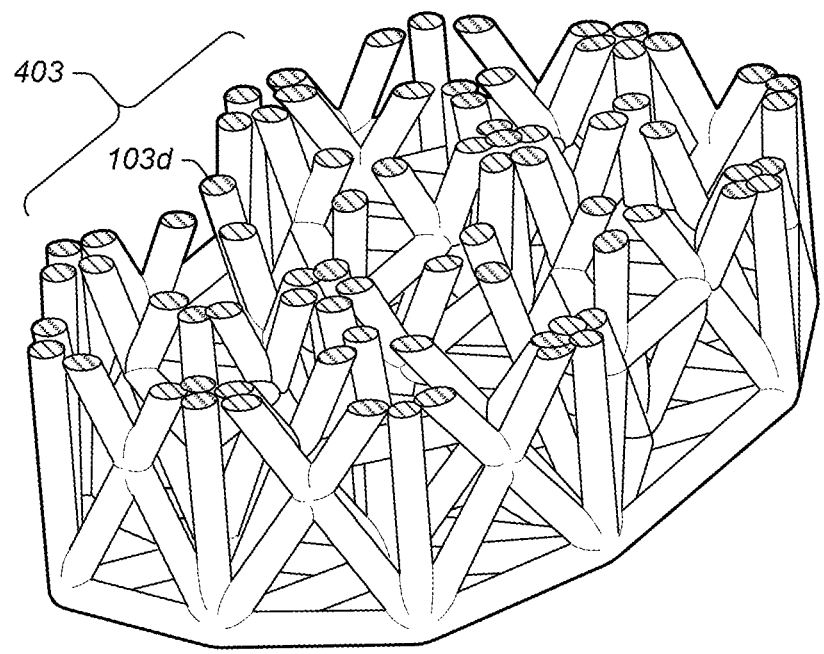
Figure 5D:
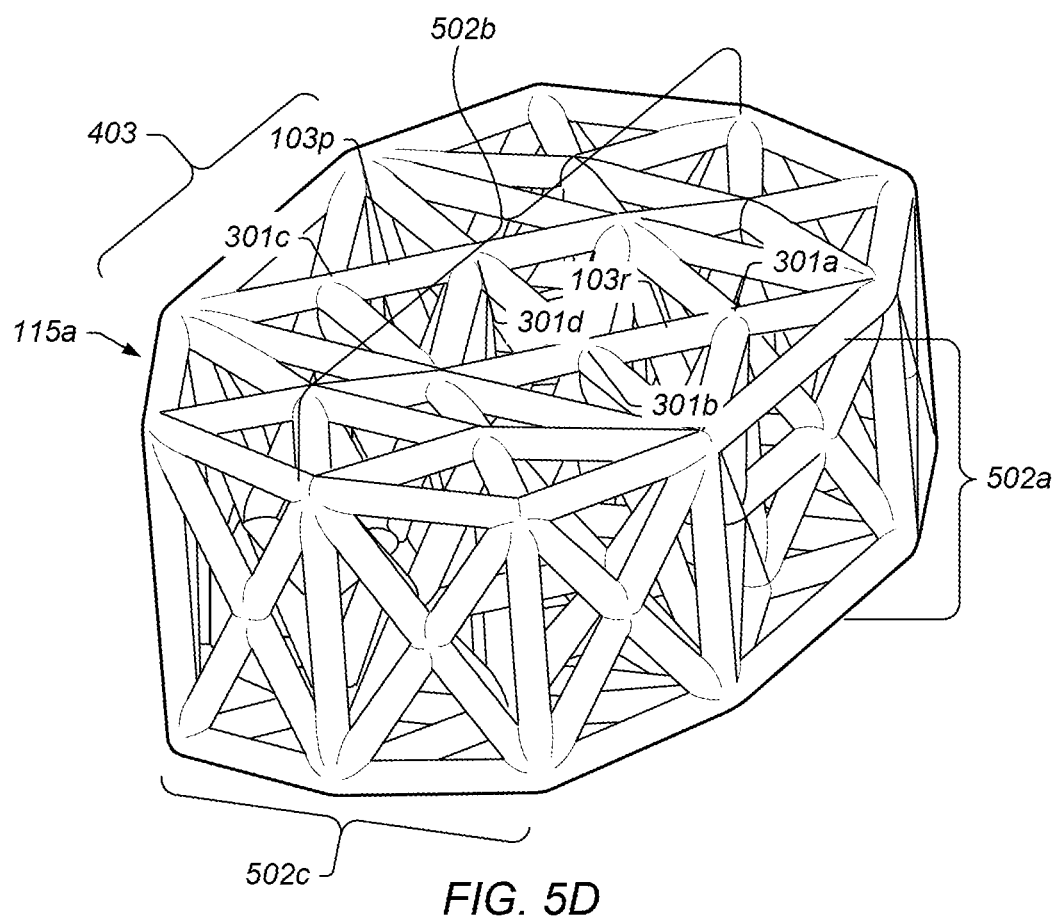
FIG. 5D illustrates an isometric view of the implant, according to an embodiment.

FIGS. 5A-5C illustrate progressive sectioned views of implant 100 showing the internal structure of implant 100, according to an embodiment. FIG. 5A illustrates a sectioned view of a lower portion of implant 100. Bottom surface 115b is shown with various struts (e.g., struts 103) extending upward from bottom surface 115b. FIG. 5B illustrates a sectioned view approximately mid-way through implant 100. Struts, such as struts 103e-f, shared by various stacked tetrahedrons in the web structure are shown. Some struts extend through central portion 501a and/or 501b of implant 100. FIG. 5B also shows central portions 501a,b of implant 100. In some embodiments, central portion 501a may include a rectangular region that has a width of approximately 50% of the implant width, a height of approximately 50% of the implant height, and a length of approximately 50% of the implant length and located in the center of implant 100. In some embodiments, central portion 501b may encompass a region (e.g., a spherical region, square region, etc.) of approximately a radius of approximately ⅛ to ¼ of the width of implant 100 around a position located approximately at one half the width, approximately one half the length, and approximately one-half the height of implant 100 (i.e., the center of implant 100). Other central portions are also contemplated. For example, the central portion may include a square region with a length of one of the sides of the square region approximately ¼ to ½ the width of implant 100 around a position approximately at one half the width, approximately one half the length, and approximately one half the height of the implant. An example height 502a, width 502b, and length 502c, is shown in FIG. 5D. In some embodiments, the height may be up to about 75 mm or more. In some embodiments, such as those used for long bone reconstruction, the width and/or length could be approximately 7 inches or longer. In some embodiments, the width, length, and/or height may vary along implant 100 (e.g., the height may vary if the implant includes lordosis). The height may be taken at one of the opposing sides, the middle, and/or may be an average of one or more heights along the length of implant 100. The web structure may extend through central portion 501a,b of the implant (e.g., at least one strut of the web structure may pass at least partially through central portion 501a,b). FIG. 5C illustrates another sectioned view showing sectioned views of top tetrahedrons in the web structure. FIG. 5D shows a complete view of implant 100 including top surface 115a with vertices 301a-d.

Figure 6A:
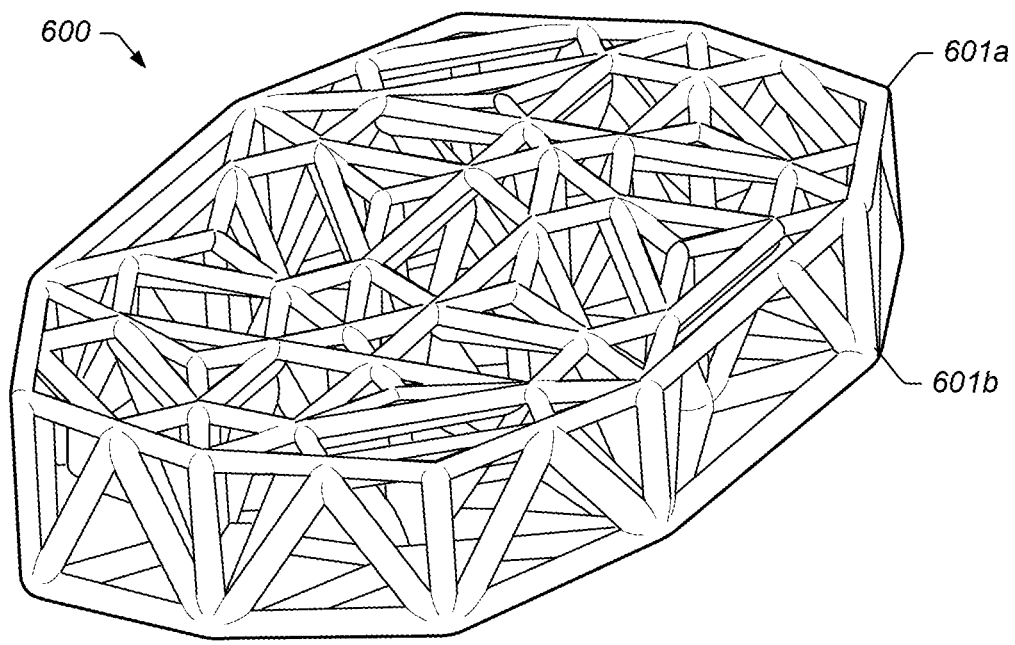
FIGS. 6A-6D illustrate another configuration of the web structure, according to an embodiment.
Figure 6B:
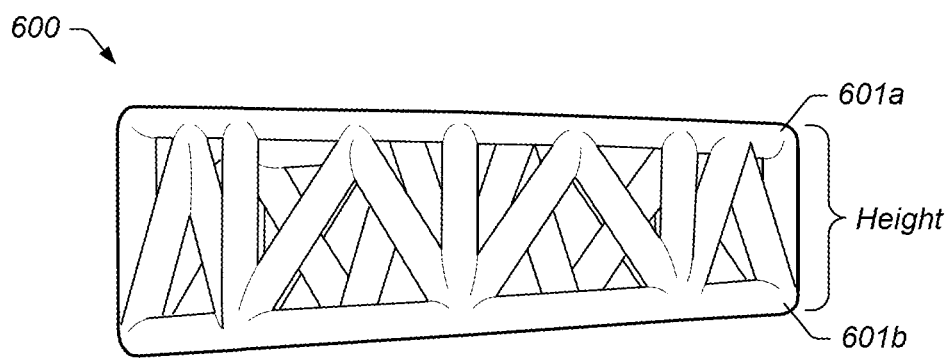

FIGS. 6A-6D illustrate alternate embodiments of implant 100. In some embodiments, different sections of the hexahedron-shaped geometric design may be used. For example, as seen in FIG. 6A, the bottom half of the hexahedron-shaped geometric design may be used (primarily including the lower tetrahedron structures). If using the bottom half of the design, design 600 may be expanded proportionately to have similar overall dimensions as the hexahedron-shaped geometric design (e.g., the tetrahedrons may be expanded to approximately twice the height of the tetrahedrons in the hexahedron-shaped geometric design to give design 600 a height approximately the same as the hexahedron-shaped geometric design). In some embodiments, design 600 may also be angled (e.g., on top surface 601*a* and/or bottom surface 601*b*) to provide design 600 with lordosis to, in some embodiments, have a better fit between the vertebral endplates. Top surface 601*a* and/or bottom surface 601*b* may also include struts to connect nodes of design 600 (e.g., see the strut network on the top surface in FIG. 6*a*). Other patterns of struts for top surface 601*a* and/or bottom surface 601*b* may also be used. In some embodiments, design 600 may not include negative angles between struts and may thus be easier to create through a casting or molding process.

Figure 6C:
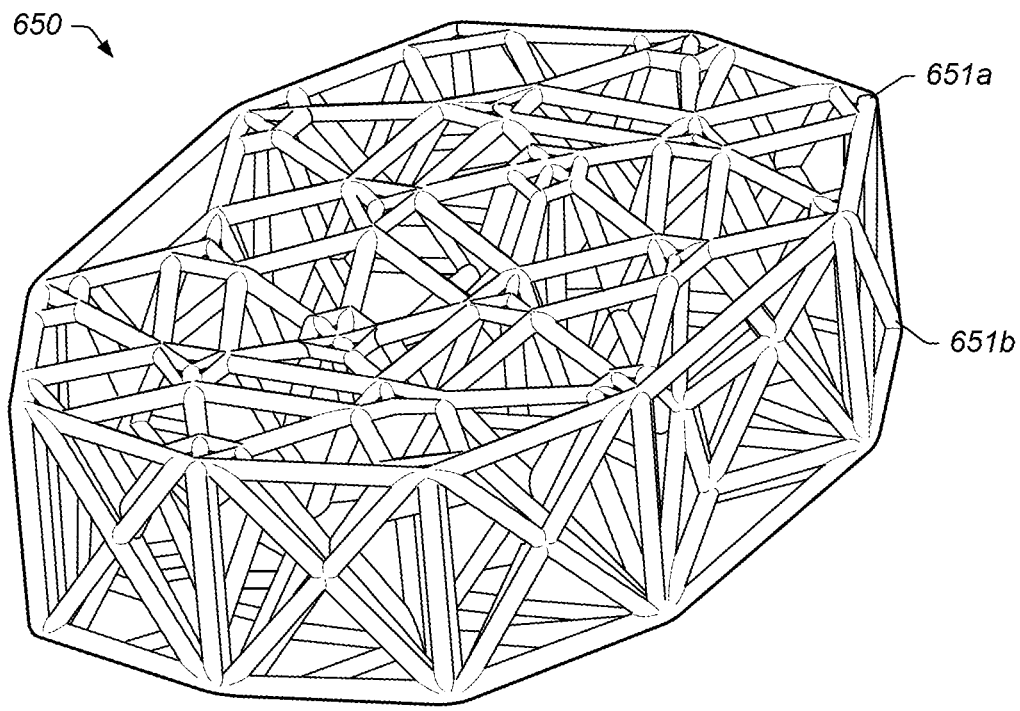
Figure 6D:
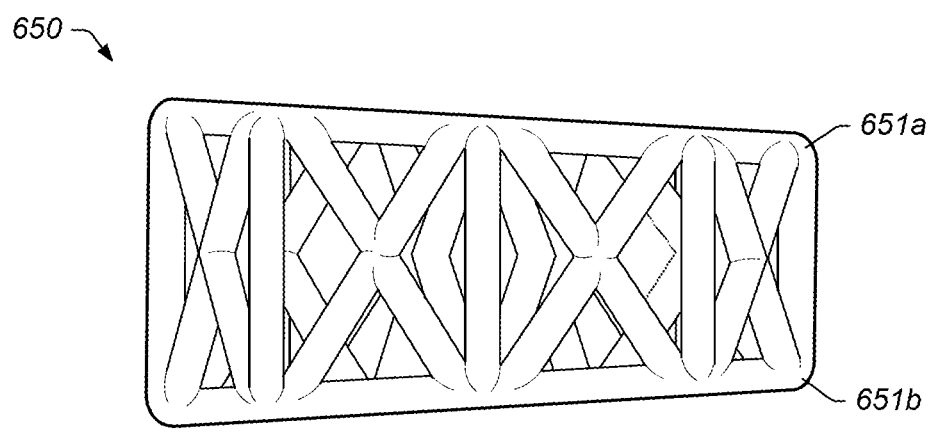

FIGS. 6C-6D illustrate another alternate embodiment of implant 100. In some embodiments, approximately the middle 40 to 60 percent of the hexahedron-shaped geometric design may be used. For example, if an overall height of the hexahedron-shaped geometric design is approximately 37 mm, approximately the bottom 10 mm and approximately the top 10 mm of the design may be removed and approximately the middle 17 mm of the design may be used for the implant. Middle portion design 650 may then be expanded proportionately such that the approximate height of the expanded design may be approximately 37 mm (or a different height as needed). Top surface 651*a* and bottom surface 651*b* may include a network of struts (e.g., see the struts on top surface 651*a* of FIG. 6C) (other networks of struts are also contemplated). Other portions of the design for the implant are also contemplated (e.g., the top half of the design shown in FIG. 1A, the bottom half of the design shown in FIG. 1A, etc). Design portions may be proportionately expanded to meet specified dimensions (e.g., specified height, width, and length). In some embodiments, the amount of struts may be reduced or material in the implant may be redistributed so that some struts may have a larger diameter and some may have a smaller diameter (e.g., the different diameters may reinforce against different directional forces). In some embodiments, a partial-design cage may be used (e.g., with half of the web structure so that the structure includes a tetrahedron. Further, in some embodiments, the implant may include angled surfaces (e.g., an angled top surface 651*a* and/or angled bottom surface 651*b*) to provide lordosis for implants to be implanted between the vertebral endplates.

In some embodiments, the web structure of implant 100 may distribute forces throughout implant 100 when implanted. For example, the connecting struts of the web structure may extend throughout the core of implant 100, and the interconnectivity of struts 103 may disperse the stress of compressive forces throughout implant 100 to reduce the potential of stress risers (the distribution of forces throughout implant 100 may prevent concentration of stress on one or more portions of the vertebrae that may otherwise result in damage to the vertebrae).

In some embodiments, the web structure of implant 100 (e.g., the external and internal struts of implant 100) may also provide surface area for bone graft fusion. For example, the web structure extending throughout implant 100 may add additional surface areas (e.g., on the surface of the struts making up implant 100) to fuse to the bone graft material and prevent bone graft material from loosening or migrating from implant 100. In some embodiments, the web structure may also support bone in-growth. For example, when implanted, adjacent bone (e.g., adjacent vertebrae if the implant is used as a spinal implant) may grow over at least a portion of struts 103 of implant 100. The bone growth and engagement between the bone growth and implant 100 may further stabilize implant 100. In some embodiments, the surfaces of implant 100 may be formed with a rough surface to assist in bone in-growth adhesion.

In some embodiments, struts 103 may have a diameter approximately in a range of about 0.025 to 5 millimeters (mm) (e.g., 1.0 mm, 1.5 mm, 3 mm, etc). Other diameters are also contemplated (e.g., greater than 5 mm). In some embodiments, the struts may have a length approximately in a range of 0.5 to 20 mm (e.g., depending on the implant size needed to, for example, fit a gap between vertebral endplates). As another example, struts may have a length approximately in a range of 30-40 mm for a hip implant. In some embodiments, the reduced strut size of the web structure may allow the open cells in implant 100 to facilitate bone growth (e.g., bone may grow through the open cells once implant 100 is implanted in the body). Average subsidence for implants may be approximately 1.5 mm within the first 3 weeks post op (other subsidence is also possible (e.g., approximately between 0.5 to 2.5 mm)). A strut size that approximately matches the subsidence (e.g., a strut size of approximately 1.5 mm in diameter and a subsidence of approximately 1.5 mm) may result in a net 0 impedance (e.g., the bone growth growing around the struts) after implant 100 has settled in the implanted position. The net 0 impedance throughout the entire surface area of the implant/vertebrae endplate interface may result in a larger fusion column of bone that may result in more stable fusion. Other fusion column sizes are also contemplated. The configuration of the implant 100 may redistribute the metal throughout the implant 100. In some embodiments, a rim may not be included on the implant 100 (in some embodiments, a rim may be included). The resulting bone growth (e.g., spinal column) may grow through the implant 100.

In some embodiments, greater than 50% of the interior volume of implant 100 may be open. In some embodiments, greater than 60%, greater than 70%, and/or greater than 80% of implant 100 may be open (e.g., 95%). In some embodiments, the open volume may be filled with bone growth material. For example, cancellous bone may be packed into an open/internal region of implant 100.

In some embodiments, at least a portion of the surfaces of implant 100 may be coated/treated with a material intend to promote bone growth and/or bone adhesion and/or an anitmicrobial agent to prevent infections. For example, in some embodiments, the surface of the struts (e.g., struts 103 forming the web structure) may be coated with a biologic and/or a bone growth factor. In some embodiments, a biologic may include a coating, such as hydroxyapatite, bone morphaginic protein (BMP), insulinlike growth factors I and II, transforming growth factor-beta, acidic and basic fibroblast growth factor, platelet-derived growth factor, and/or similar bone growth stimulant that facilitates good biological fixation between the bone growth and a surface of the implant. In some embodiments, a bone growth factor may include a naturally occurring substance capable of stimulating cellular growth, proliferation and cellular differentiation (e.g., a protein or steroid hormone).

In some embodiments, a biologic and/or growth factor may be secured to a central region of implant 100. For example, in some embodiments, a biologic or growth factor may be provided on at least a portion of a strut that extends through central portion 501*a* and/or 501*b* of implant 100. Such an embodiment may enable the delivery of a biologic and or a growth factor to a central portion of an implant. For example, the biologic or growth factor may be physically secured to a strut in a central portion of implant 100 as opposed to being packed into an open volume that does not include a strut provided therein for the physical attachment of the biologic and/or growth factor.

As implant 100 settles into the implant site, subsidence may place additional pressure on the bone graft material (which may already be under compressive forces in implant 100) and act to push the bone graft material toward the sides of implant 100 (according to Boussinesq's theory of adjacent material, when a force is applied to a member that is adjacent to other materials (such as sand, dirt, or bone graft material) the force against the member creates a zone of increased pressure (e.g., 60 degrees) in the adjacent material). Struts 103 of the web structure may resist bone graft material protrusion from the sides of the web structure and may increase the pressure of the bone graft material. Bone graft material may need to be implanted in a higher-pressure environment to create an environment conducive to strong bone growth (e.g., according to Wolf's law that bone in a healthy person or animal will adapt to the loads it is placed under). The web structure may thus increase the chance of stronger fusion.

Figure 7A:
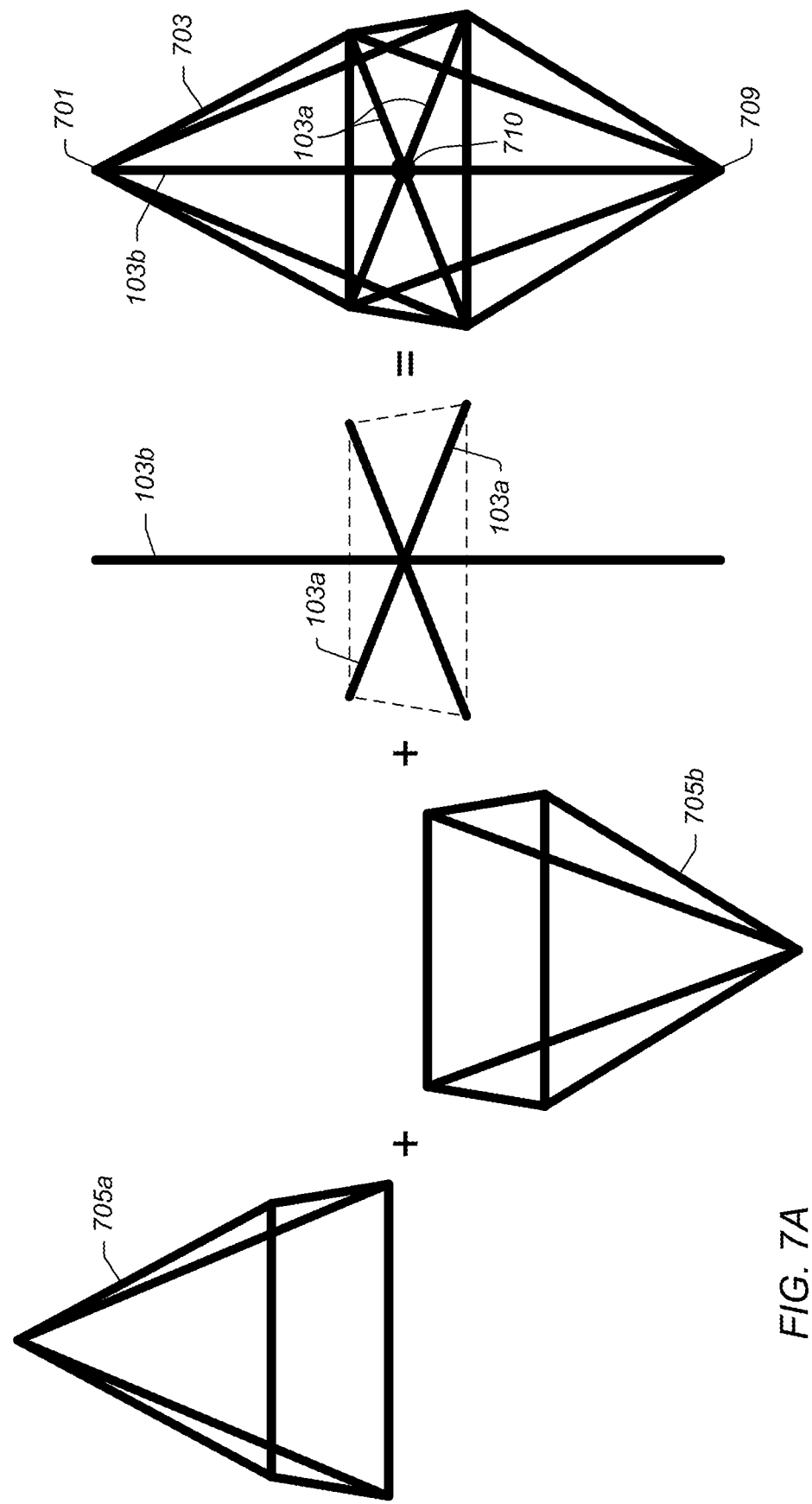
FIG. 7A illustrates a web structure formed with two pyramids, according to an embodiment.

FIG. 7A illustrates a web structure formed with two pyramids, according to an embodiment. The geometric building blocks for implant 100 include pyramids. For example, top/upper pyramid 705a and bottom/lower pyramid 705b may be joined to form a octahedron building block 703. The octahedron building blocks 703 may be joined, for example, at a face (e.g., a base 706 of the top and bottom pyramids 705a and 705b) by sharing a surface, etc. In one embodiment one or both of top and bottom pyramid 705a,b may include a square pyramid. The resulting octahedron thus includes two opposing pyramid shaped truss structures that share a common square shaped truss unit at their base (e.g., where the two bases of the pyramids meet).

It is further noted that the geometric building block may include one or more additional struts extending through an interior region defined by the faces of the building blocks. For example, in the illustrated embodiment, the octahedron building block formed from top and lower pyramids 705a,b include two struts 103a extending diagonally between opposing vertices of the face (e.g., the square shaped truss unit) shared by top and lower pyramids 705a,b, and having an intersection 710. Accordingly, the opposing vertices are directly connected by one or more struts arranged in a substantially straight line between each pair of the opposing vertices. In one embodiment, struts 103a may be formed from four separate strut sections that extend from each respective vertex to intersection 710. The illustrated embodiment also includes an additional central strut 103b that extends between vertices 701, 709 of top and bottom pyramids 705a,b, and that intersects struts 103a at or near intersection 710. In one embodiment, strut 103b may be formed from one or two separate strut sections that extend from each respective vertex 701, 709 of top and bottom pyramids 705a,b to intersection 710. Accordingly, the opposing vertices of the octahedron that do not lie in the common face (e.g. base) of the two pyramids 705a,b forming the octahedron are directly connected by one or more struts arranged in a substantially straight line between the opposing vertices. Other embodiments may include any combination of struts 103a,b. For example, one embodiment may include only one or two of struts 103a extending between opposing vertices of the square shaped common truss unit and without strut 103b. For example, one embodiment may include only two opposing vertices of the square shaped common truss unit being connected to one another via a strut. One embodiment may include only strut 103b extending between the opposing vertices of the octahedron without struts 103a.

Figure 7B:
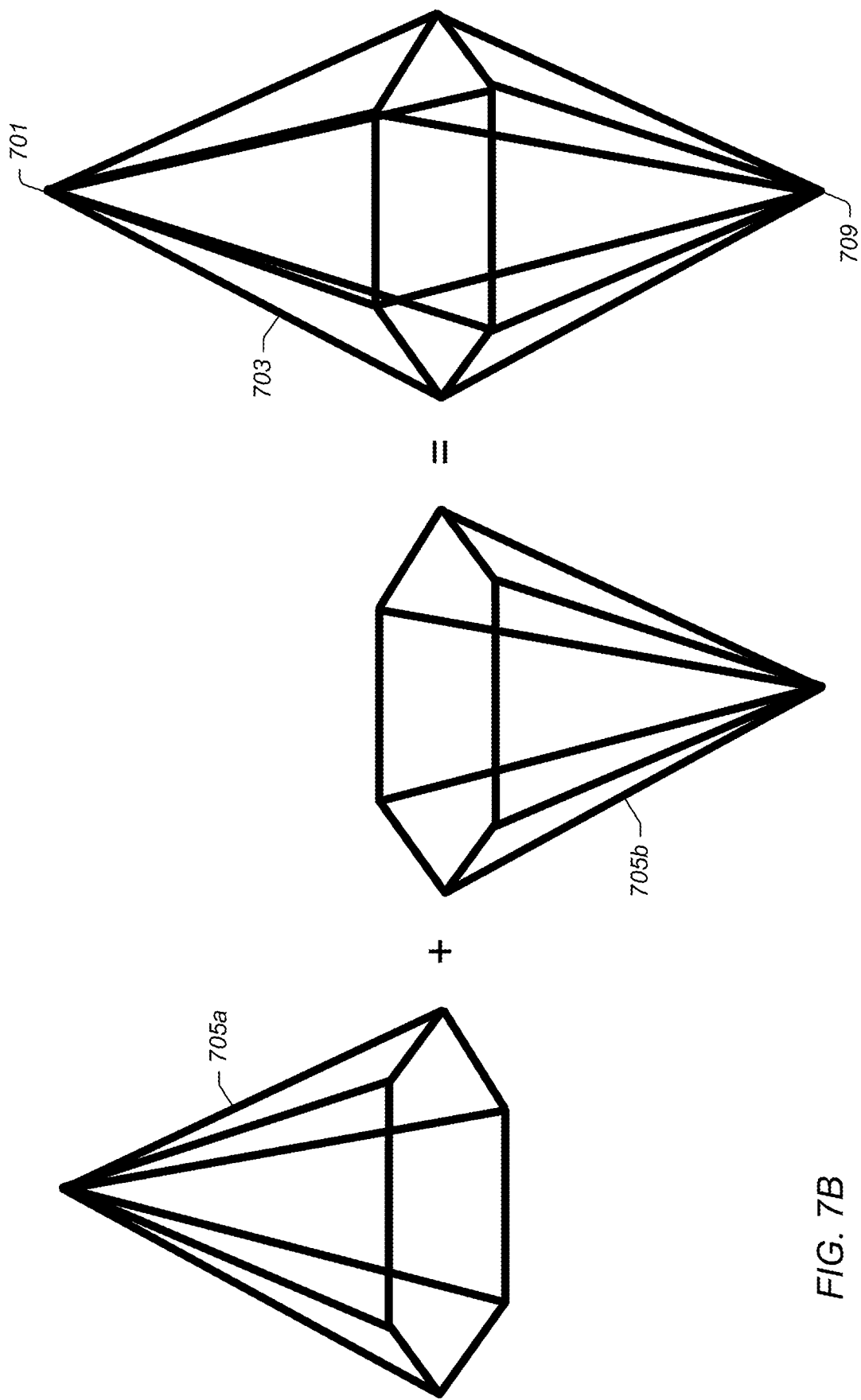
FIG. 7B illustrates a web structure formed with two heptahedrons, according to an embodiment.

FIG. 7B illustrates a web structure formed with two heptahedrons, according to an embodiment. The geometric building blocks for implant 100 include heptahedrons. For example, top/upper heptahedron 705a and bottom/lower heptahedron 705b may be joined to form a dodecahedron building block 703. The dodecahedron building blocks 703 may be joined, for example, at a face (e.g., their bases) by sharing a side surface, etc. Embodiments may include additional members, such as struts 103a,b that extend between vertices of the heptahedron 705a,b in a manner similar to that described with respect to FIG. 7A.

Figure 7C:
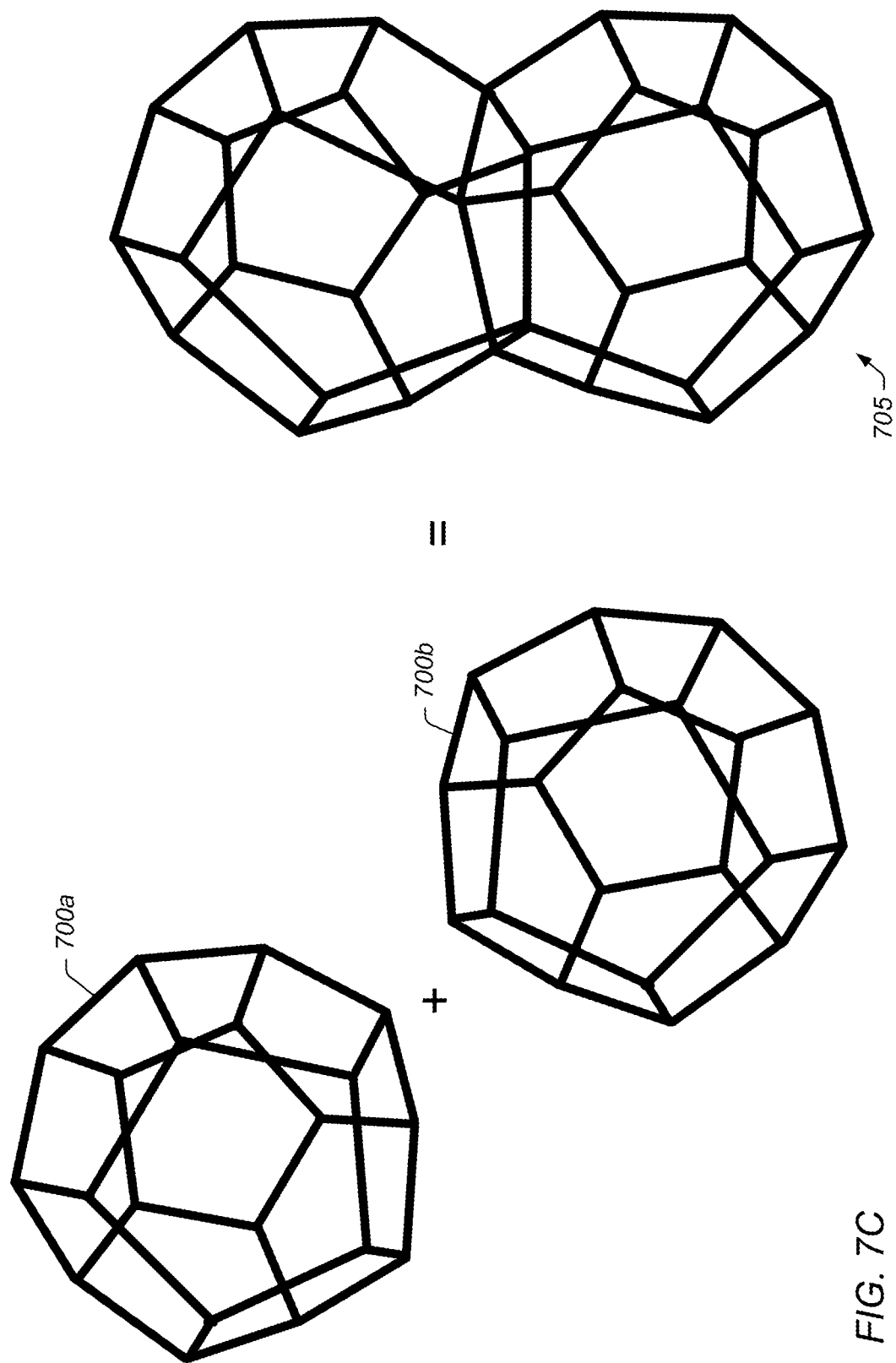
FIG. 7C illustrates a web structure formed with two dodecahedrons, according to an embodiment.

FIG. 7C illustrates a web structure formed with two dodecahedrons, according to an embodiment. For example, top/upper dodecahedron 705a and bottom/lower dodecahedron 705b may be joined to form a 22-sided polyhedron building block 703. The 22-sided polyhedron building blocks 703 may be joined, for example, at a face by sharing a side surface, etc. Embodiments may include additional members, such as struts 103a,b that extend between vertices of the dodecahedrons 705a,b in a manner similar to that described with respect to FIG. 7A.

Web structures formed from other truss configurations are also contemplated. For example, the trusses may include a series of packing triangles, a two-web truss, a three-web truss, etc. Further, the web structure for implant 100 may include one or more trusses as described in U.S. Pat. No. 6,931,812 titled "Web Structure and Method For Making the Same", which issued Aug. 23, 2005, which is hereby incorporated by reference in its entirety as though fully and completely set forth herein.

Figure 10:
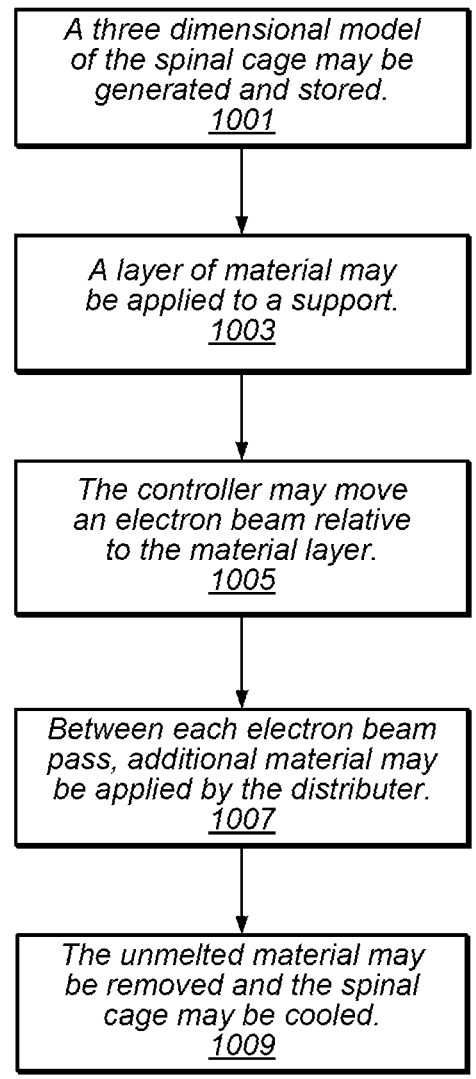
FIG. 10 illustrates a flowchart of a method for making an implant, according to an embodiment.
Figure 11C:
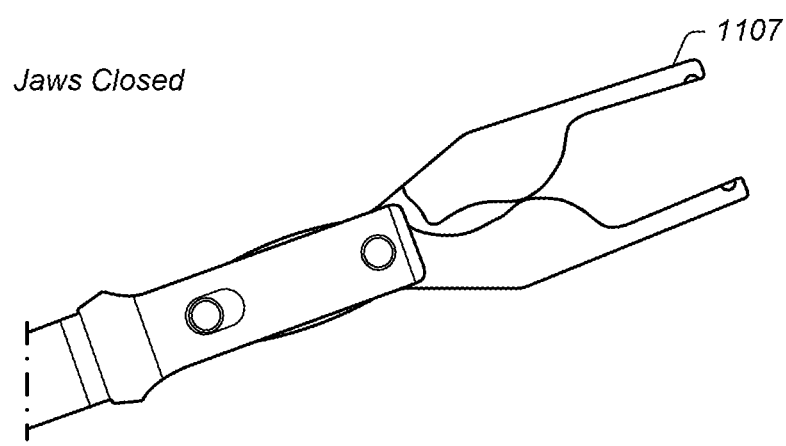
Figure 11D:
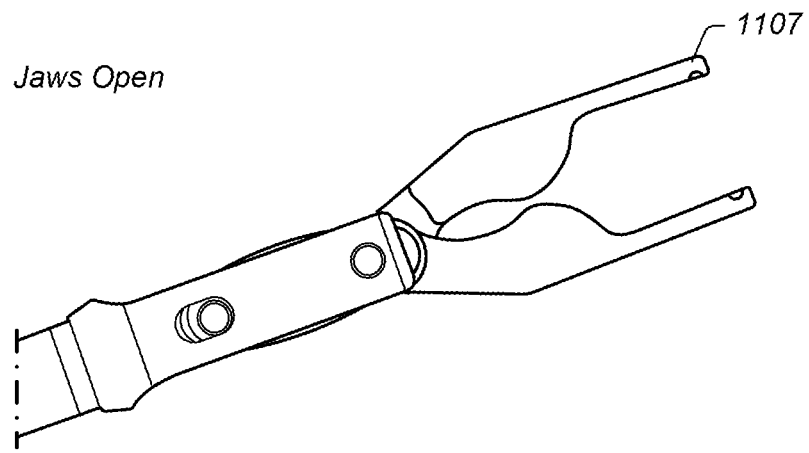

FIG. 10 illustrates a flowchart of a method for making implant 100. In some embodiments, implant 100 may be made through rapid prototyping (e.g., electron beam melting, laser sintering, etc). It should be noted that in various embodiments of the methods described below, one or more of the elements described may be performed concurrently, in a different order than shown, or may be omitted entirely. Other additional elements may also be performed as desired. In some embodiments, a portion or the entire method may be performed automatically by a computer system.

At 1001, a three dimensional model of implant 100 may be generated and stored in a storage medium accessible to a controller operable to control the implant production process. At 1003, a layer of material (e.g., a powder, liquid, etc.) may be applied to a support. In some embodiments, the powder may include γTiAl (γTitanium Aluminides) which may be a high strength/low weight material. Other materials may also be used. The powder may be formed using a gas atomization process and may include granules with diameters approximately in a range of 20 to 200 micrometers (μm) (e.g., approximately 80 μm). The powder may be delivered to the support through a distributer (e.g., delivered from a storage container). The distributer and/or the support may move during distribution to apply a layer (e.g., of powder) to the support. In some embodiments, the layer may be approximately a uniform thickness (e.g., with an average thickness of 20 to 200 micrometers (μm)). In some embodiments, the distributer and support may not move (e.g., the material may be sprayed onto the support). At 1005, the controller may move an electron beam relative to the material layer. In some embodiments, the electron beam generator may be moved, and in some embodiments the support may be moved. If the material is γTiAl, a melting temperature approximately in a range of 1200 to 1800 degrees Celsius (e.g., 1500 degrees Celsius) may be obtained between the electron beam and the material. At 1007, between each electron beam pass, additional material may be applied by the distributer. At 1009, the unmelted material may be removed and implant 100 may be cooled (e.g., using a cool inert gas). In some embodiments, the edges of the implant may be smoothed to remove rough edges (e.g., using a diamond sander). In some embodiments, the implant may include rough edges to increase friction between the implant and the surrounding bone to increase adhesion of the implant to the bone.

Other methods of making implant 100 are also contemplated. For example, implant 100 may be cast or injection molded. In some embodiments, multiple parts may be cast or injection molded and joined together (e.g., through welding, melting, etc). In some embodiments, individual struts 103 forming implant 100 may be generated separately (e.g., by casting, injection molding, etc.) and welded together to form implant 100. In some embodiments, multiple implants of different sizes may be constructed and delivered in a kit. A medical health professional may choose an implant (e.g., according to a needed size) during the surgery. In some embodiments, multiple implants may be used at the implant site.

Figure 12:
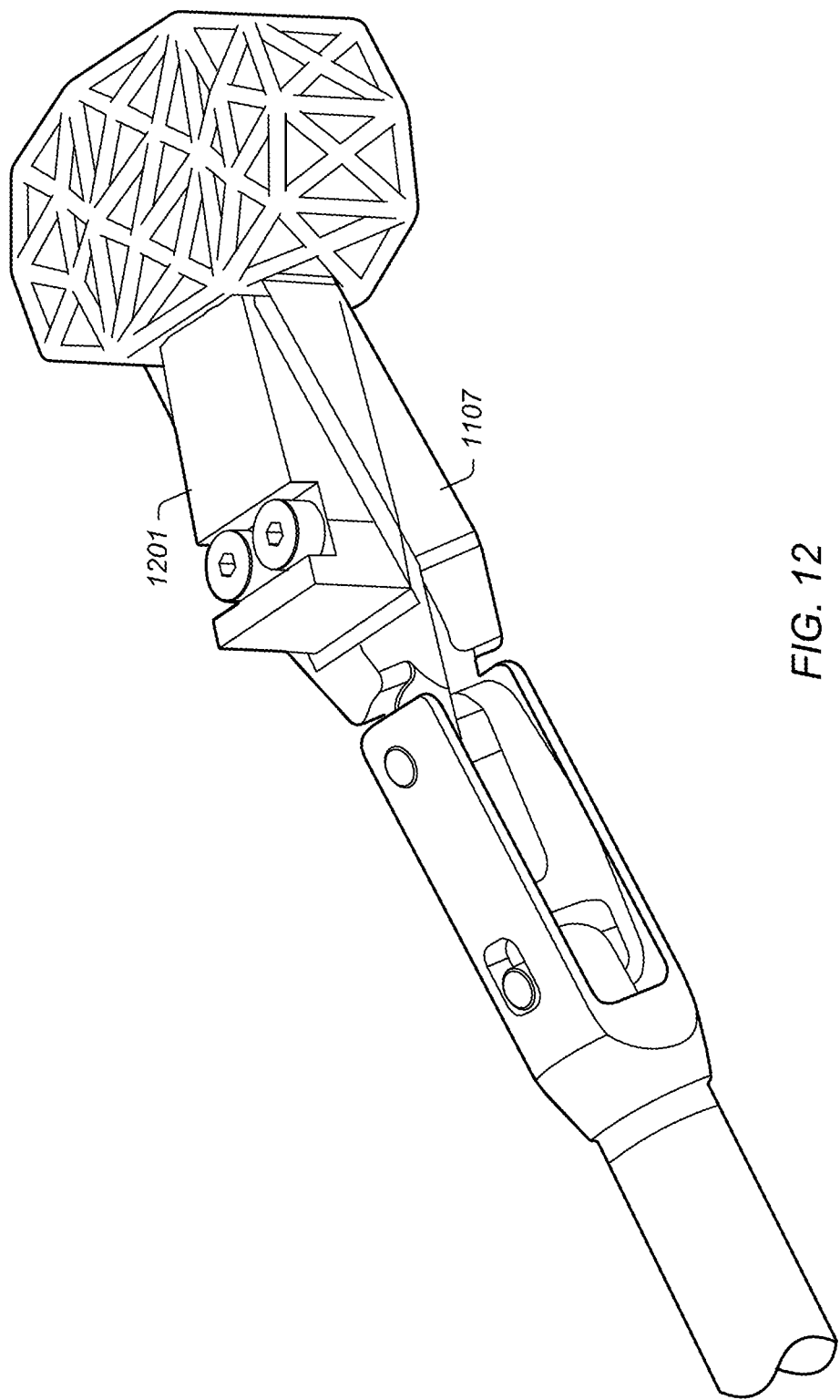
FIG. 12 illustrates an implant handler gripping an implant, according to an embodiment.

FIGS. 11A-11D illustrate various views of implant handler 1100, according to an embodiment. In some embodiments, handler 1100 may include jaws 1107 to grip and release implant 100. Jaws 1107 may be operated by trigger 1109 coupled to cam 1115 that acts to push block 1101 when trigger 1109 is pushed away from handle 1117. In some embodiments, leaf spring 1111 may act to push trigger 1109 away from handle 1117. As block 1101 is pushed by cam 1115, block 1101 may push against compression spring 1103 and shaft 1105 (which may be flexible shaft inside tube 1119). Shaft 1105 may push against jaws 1107 and push them open (see FIG. 11D). As trigger 1109 is pulled toward handle 1117, the force on block 1101 may be released and coil compression spring 1103 may push block 1101 toward handle 1117. Shaft 1105 may also be pulled with block 1101 toward handle 1117 (in some embodiments, shaft 1105 may be coupled to block 1101). As shaft 1105 is pulled toward handle 1117, shaft 1105 may pull jaws 1107 closed (e.g., see FIGS. 11c and 12) such that struts of implant 100 may be gripped in grooves 1119 in jaws 1107 (e.g., see FIG. 12 which illustrates handler 1100 gripping implant 100). In some embodiments, block 1201 (see FIG. 12) may be gripped between jaws 1107 and at least partially in contact with implant 100 to at least partially distribute forces from a hammer (used to implant the implant 100) over a greater contact area on implant 100 (to prevent a concentration of impact force on a limited number of struts). Handler 1100 is one embodiment of a handler for implant 100; other handlers and handler types are also contemplated.

Figure 13:
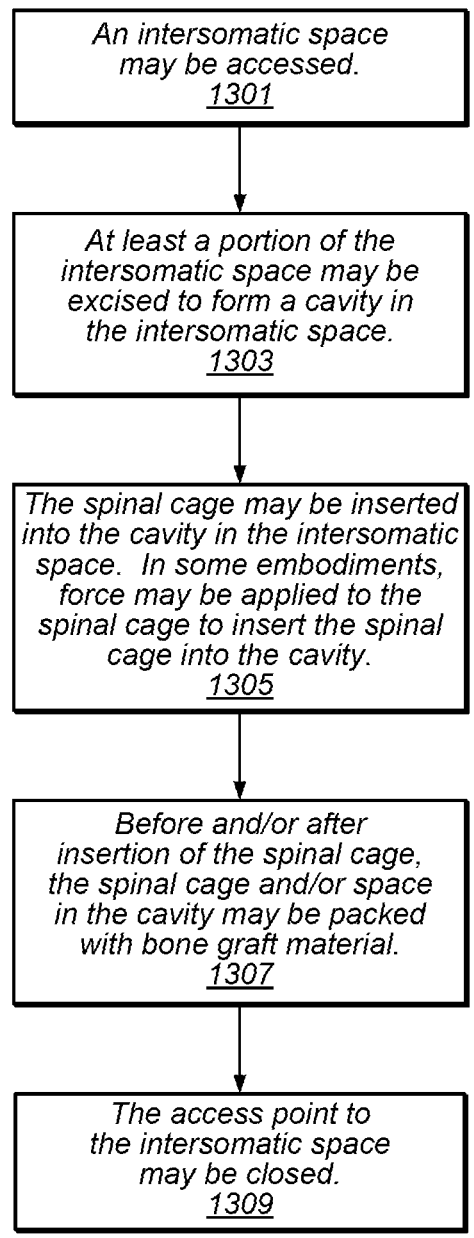
FIG. 13 illustrates a flowchart of a method for implanting a spinal implant, according to an embodiment.

FIG. 13 illustrates a flowchart of a method for implanting a spinal implant, according to an embodiment. It should be noted that in various embodiments of the methods described below, one or more of the elements described may be performed concurrently, in a different order than shown, or may be omitted entirely. Other additional elements may also be performed as desired. In some embodiments, a portion or the entire method may be performed automatically by a computer system.

At step 1301, an intersomatic space may be accessed. For example, an anterior opening may be made in a patient's body for an anterior lumbar inter-body fusion (ALIF) approach or a posterior opening may be made for a posterior lumbar inter-body fusion (PLIF) approach. At 1303, at least a portion of the intersomatic space may be excised to form a cavity in the intersomatic space. At 1305, the implant may be inserted into the cavity in the intersomatic space. In some embodiments, handler 1100 may be used to grip implant 100. In some embodiments, force may be applied to the implant (e.g., through a hammer) to insert the implant into the cavity. After placement of implant 100, trigger 1109 on handler 1100 may be released to release implant 100. At 1307, before and/or after insertion of the implant, the implant and/or space in the cavity may be packed with bone graft material. At 1309, the access point to the intersomatic space may be closed (e.g., using sutures).

Figure 14:
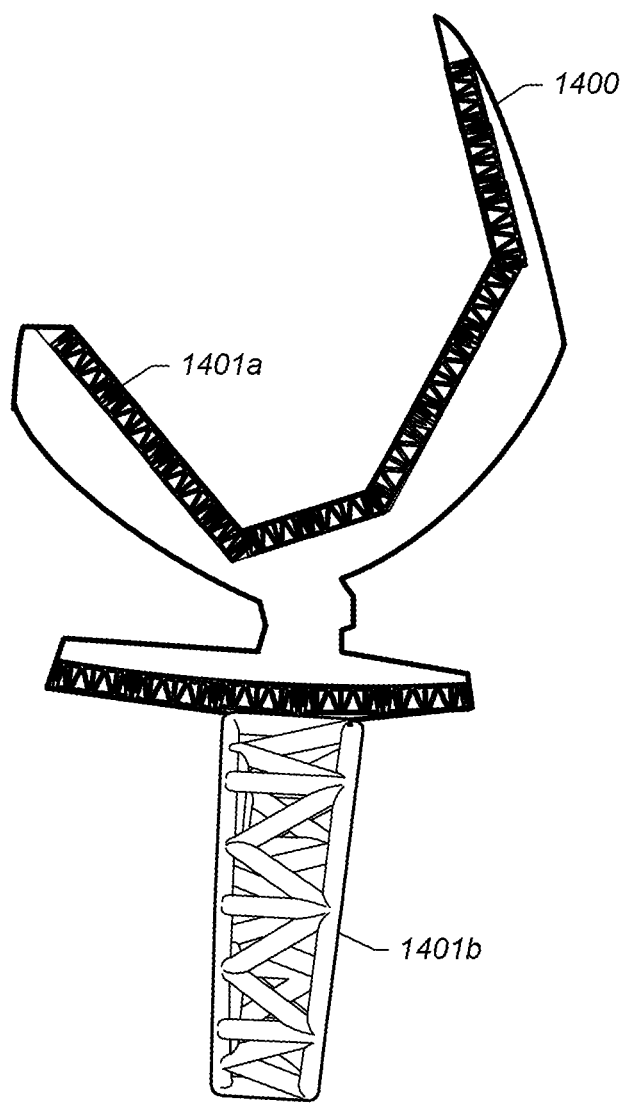
FIG. 14 illustrates a knee replacement implant that includes the web structure, according to an embodiment.

FIG. 14 illustrates knee replacement implant 1400 that includes a web structure, according to an embodiment. In some embodiments, portions of knee replacement implant 1400 may include a web structure to, for example, increase bone graft fusion with surrounding bone (e.g., along portions of implant 1400 that are anchored in the bone). Portion 1401a and 1401b may include the web structure for bone in-growth to further support and secure the knee implant. Other portions of knee implant 1400 may also include a web structure.

Figure 15:
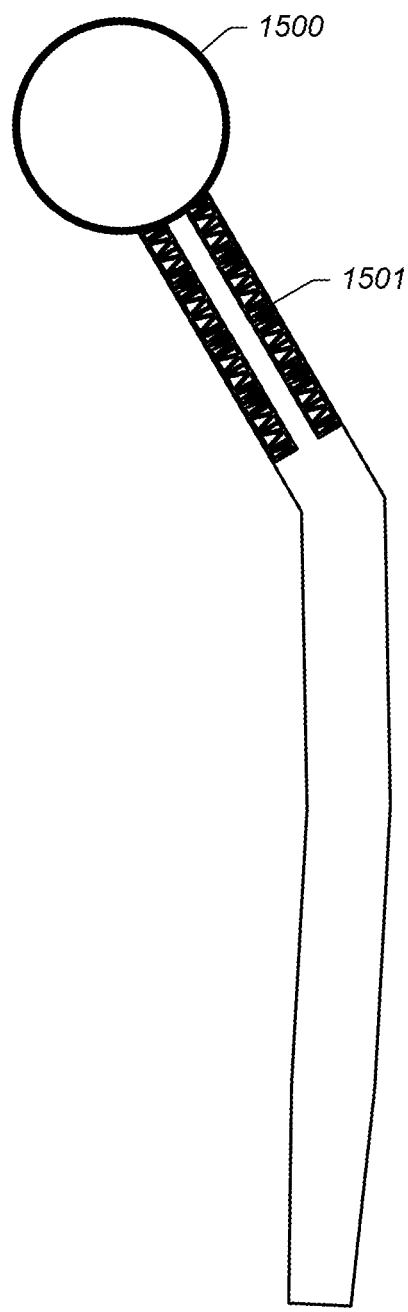
FIG. 15 illustrates a hip replacement implant that includes the web structure, according to an embodiment.

FIG. 15 illustrates hip replacement implant 1500 that includes a web structure, according to an embodiment. Portions of shaft 1501 of hip implant 1500 may include a web structure for bone in-growth along the shaft to support and secure the hip implant 1500. In some embodiments, implant 1500 may use a web structure in place of (or in addition to) texture along shaft 1501 for securing implant 1500.

Figure 16:
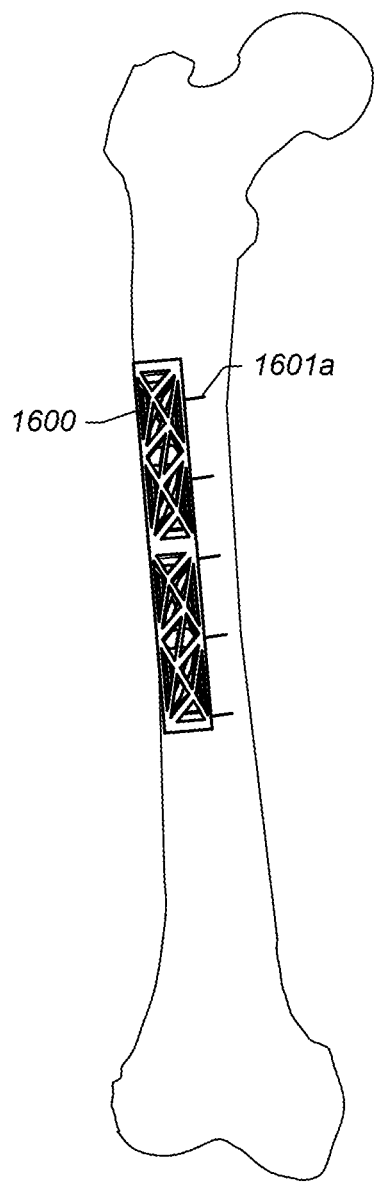
FIG. 16 illustrates a long bone reconstruction implant that includes the web structure, according to an embodiment.

FIG. 16 illustrates long bone reconstruction implant 1600 that includes a web structure, according to an embodiment. In some embodiments, a web structure may be used in implant 1600 for securing a long bone (e.g., the femur or tibia). For example, if the long bone has a compound fracture, the implant may be fastened to the bone along the bone (e.g., using bone screws 1601) to keep the bone segments in place during healing. The bone may also grow into the implant web structure to further secure the implant to the long bone. Other bones are also contemplated (e.g., clavicle, phalanges, metatarsals, etc). The implant may be coated and/or infused with a biologic material to encourage bone growth or an antimicrobial agent to reduce the chance of infection.

Figure 17:
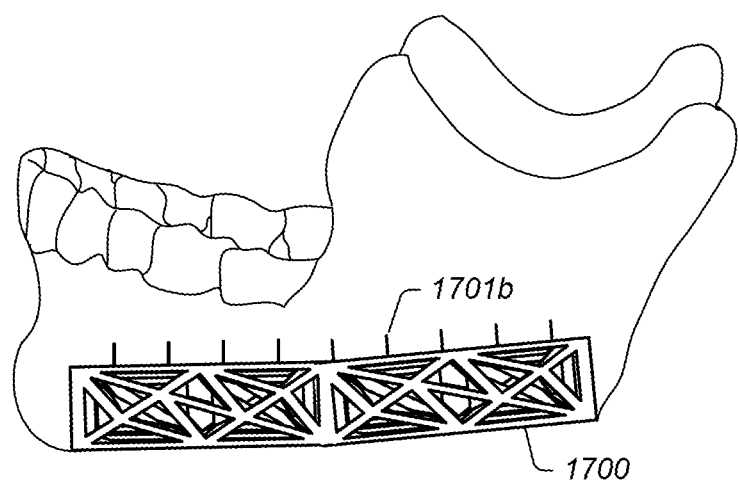
FIG. 17 illustrates a cranio-maxifacial implant that includes the web structure, according to an embodiment.

FIG. 17 illustrates cranio-maxifacial implant 1700 that includes a web structure, according to an embodiment. In some embodiments, implant 1700 may be used to reconstruct a portion of the jaw. The top and bottom surfaces of implant 1700 may include additional struts (e.g., as seen in FIG. 1A) or may include point junctions (e.g., as seen in FIG. 2D). Implant 1700 may be secured to the implant site (e.g., through bone screws 1701) or may be self securing (e.g., between two or more bones).

In some embodiments, the implant may be customized. For example, three dimensional measurements and/or shape of the implant may be used to construct an implant that distributes the web structure throughout a three-dimensional shape design. As noted in FIG. 10, the three-dimensional shape design of the implant may be entered into a computer system/controller that may control the electron beam melting process. In some embodiments, the truss design and orientation may be preset or predetermined by the computer system/controller. In some embodiments, a user may select the truss design to use (e.g., one or more of truss designs shown in FIG. 3A, 7A, or 8A-9) and/or may select the orientation of the trusses in the implant. In some embodiments, the user may enter the outer dimensions of the three dimensional shape and the computer system/controller may generate a three-dimensional design that includes the truss design and orientation. The computer system/controller may generate the three-dimensional design by providing a uniform distribution of the truss design throughout a three-dimensional shape with the outer dimensions provided by the user. In some embodiments, the heights and widths of the trusses used in the design may be proportional to the overall height and width of the three-dimensional shape (e.g., the trusses may have heights approximately equal to ½ the overall height and a width of approximately 1/16 the overall width). Other heights and widths are also contemplated. In some embodiments, the user may provide the height and width and/or the computer system/controller may have default heights and widths to use.

Embodiments of a subset or all (and portions or all) of the above may be implemented by program instructions stored in a memory medium or carrier medium and executed by a processor (e.g., a processor on the controller operable to control the implant production process). A memory medium may include any of various types of memory devices or storage devices. The term "memory medium" is intended to include an installation medium, e.g., a Compact Disc Read Only Memory (CD-ROM), floppy disks, or tape device; a computer system memory or random access memory such as Dynamic Random Access Memory (DRAM), Double Data Rate Random Access Memory (DDR RAM), Static Random Access Memory (SRAM), Extended Data Out Random Access Memory (EDO RAM), Rambus Random Access Memory (RAM), etc.; or a non-volatile memory such as a magnetic media, e.g., a hard drive, or optical storage. The memory medium may comprise other types of memory as well, or combinations thereof. In addition, the memory medium may be located in a first computer in which the programs are executed, or may be located in a second different computer that connects to the first computer over a network, such as the Internet. In the latter instance, the second computer may provide program instructions to the first computer for execution. The term "memory medium" may include two or more memory mediums that may reside in different locations, e.g., in different computers that are connected over a network.

In some embodiments, a computer system at a respective participant location may include a memory medium(s) on which one or more computer programs or software components according to one embodiment of the present invention may be stored. For example, the memory medium may store one or more programs that are executable to perform the methods described herein. The memory medium may also store operating system software, as well as other software for operation of the computer system.

In some embodiments, a truss/web structure may be disposed on at least a portion of an implant to facilitate coupling of the implant to an adjacent structure. For example, where an implant is implanted adjacent a bony structure, one or more truss structures may be disposed on and/or extend from a surface (e.g., an interface plate) of the implant that is intended to contact, and at least partially adhere to, the bony structure during use. In some embodiments, such as those including an intervertebral implant disposed between the end plates of two adjacent vertebrae during use, one or more truss structures may be disposed on a contact surface of the intervertebral implant to facilitate bone growth that enhances coupling of the intervertebral implant to the bony structure. For example, a truss structure may include one or more struts that extend from the contact surface to define an open space for bone growth therethrough, thereby enabling bone through growth to interlock the bone structure and the truss structure with one another to couple the implant to the bony structure at or near the contact face. Such interlocking bone through growth may inhibit movement between the implant and the bony structure which could otherwise lead to loosening, migration, subsidence, or dislodging of the implant from the intended position. Similar techniques may be employed with various types of implants, including those intended to interface with tissue and/or bone structures. For example, a truss structure may be employed on a contact surface of knee implants, in a corpectomy device, in a hip replacement, in a knee replacement, in a long bone reconstruction scaffold, or in a cranio-maxifacial implant hip implants, jaw implant, an implant for long bone reconstruction, foot and ankle implants, shoulder implants or other joint replacement implants or the like to enhance adherence of the implant to the adjacent bony structure or tissue.

Figure 18:
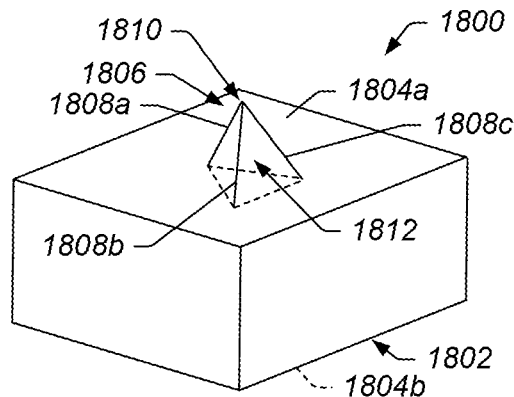
FIG. 18 illustrates a truss structure disposed on an implant, according to an embodiment.

FIG. 18 depicts an embodiment of an implant 1800 in accordance with one or more embodiments of the present technique. In some embodiments, implant 1802 may include a spinal implant, a knee implant, a hip implant, a jaw implant, an implant for long bone reconstruction, or the like. In one such embodiment, implant 1800 may include an intervertebral implant that is to be implanted between end plates of two adjacent vertebras during a spinal implant procedure. For example, implant 1800 may include a fusion implant (e.g., a fusion cage) intended to rigidly fix the relative positions of the two adjacent vertebrae, or and dynamic intervertebral device intended to couple to each of the two adjacent vertebrae and to facilitate motion (e.g., flexion, extension, and/or lateral bending) between the two adjacent vertebrae.

In the illustrated embodiment, implant 1800 includes a body 1802 having two contact faces 1804a,b. As used herein, the term "contact face" refers to a portion of an implant intended to be in contact or near contact with an adjacent structure (e.g., a bony structure) to adhere/couple with the adjacent structure when implanted. A contact surface may include an interface plate of an implant, for instance. An implant may include any number of contact faces. For example an implant may include one or more contact faces intended to couple to one or more adjacent bony structures. As depicted, in some embodiments, contact face 1804a may include an upper contact face intended to contact and secure to a first adjacent bony structure, and 1804b may include a lower contact face intended to contact and secure to a second adjacent bony structure. For example, where implant 1800 is intended to sandwich between two adjacent bony structures (e.g., end plates of two adjacent vertebrae), contact face 1804a may couple to a portion of the first bony structure disposed above implant 1800 and contact face 1804b may couple to the second bony structure disposed below implant 1800. It will be appreciated that the number and orientation of the contact surfaces may vary based on the intended application, and, thus, relative terms such as upper and lower are intended as exemplary and are not intended to be limiting. For example, one or both of the upper and lower contact faces 1804a,b may be oriented such that the are disposed laterally (e.g., as right, left, back and/or front sides of implant body 1802. Moreover, the cubic shape of body 1802 is intended to be exemplary and is not intended to be limiting. For example, body 1802 may include any desirable implant construct such as fusion cages with different shapes or a mechanical construct that allows for motion preservation. Contact surface(s) may take any suitable shape, e.g., a substantially flat planar surface, a curved/contoured surface, ridges, or the like.

In some embodiments, a single, a plurality or all of the contact faces of an implant may include one or more truss structures. For example, in the illustrated embodiment, upper contact face 1804a includes a truss structure 1806 disposed thereon. Such an embodiment may be of particular use when implant 1800 is intended to create a fixation for a tibila tray and femoral component for a knee replacement implant or any other joint replacement implant. It will be appreciated that although truss structure 1806 is illustrated on a single contact surface, other embodiments may include any number of truss structures disposed on any number of contact faces. For example, in some embodiments, implant 1800 may include one or more truss structures 1806 disposed on one or both of upper and lower contact surfaces 1804a,b. Such an embodiment may be of particular use when implant 1800 is intended to span the distance between two adjacent bony structures (e.g., the end plates of two adjacent vertebrae).

In some embodiments, a truss structure includes one or more struts that extend from a respective contact surface and defines an opening that enables bone through growth to facilitate coupling of the truss structure and the implant to the boney structure. For example, in the illustrated embodiment, truss structure 1806 includes a space truss formed of three struts 1807a,b,c that each include elongate members each having a first end coupled to contact surface 1804a and a second end coupled to each of the other struts at a vertex 1810. Each face of the triangular shaped truss structure includes a planar truss structure having a triangular opening with a perimeter defined by two of struts 1807a,b,c and the adjacent portion of contact face 1804a. As depicted, truss structure 1806 includes a generally triangular shaped space truss that defines a four sided, substantially open volume 1812.

In some embodiments, open volume 1812 may facilitate bone growth through truss structure 1806, thereby enhancing coupling of implant 1800 to the adjacent bony structure. For example, in some embodiments, at least a portion of truss structure 1806 is in contact or near contact with the adjacent bony structure, thereby enabling bone growth to extend into and/or through at least a portion of open volume 1812 of truss structure 1806 such that the bone growth interlocks with one or more struts 1808a,b,c of truss structure 1806. The interlocking of the bone growth and the struts may rigidly fix implant 1800 in a fixed location relative to the boney structure.

In some embodiments, implant 1800 may be pressed into contact with the adjacent bony structure such that at least a portion of truss structure 1806 is disposed inside of the adjacent bony structure upon implantation. For example, in some embodiments, implant 1800 may be pressed into contact with the adjacent bony structure such that vertex 1810 pierces into the bony structure and is advanced such that at least a portion of struts 1808a,b,c and open volume 1812 extend into the bony structure. Such a technique may encourage bone to grow into and/or through open volume 1812. In some embodiments, implant 1800 may be advanced/pressed into the adjacent bony structure until the respective contact surface (e.g., upper contact surface 1804a) is in contact or near contact with the adjacent bony structure. In some embodiments, at least a portion of the truss structure and/or the contact surface may be coated/treated with a material intend to promote bone growth and/or bone adherence and an antimicrobial to prevent infection to the truss structure and/or the contact surface. For example, in some embodiments, the surface of the struts and/or the contact surface may be coated with a biologic and/or a bone growth factor, such as those described herein.

Figure 19:
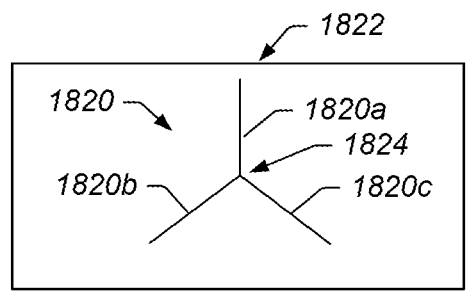
FIG. 19 illustrates a cut made into a boney structure, according to an embodiment.

In some embodiments, at least a portion of the adjacent bony structure in which the truss structure is to be implanted may be pierced/cut/slit prior to truss structure 1806 being advanced/pressed into the adjacent bony structure. In some embodiments, a cutting tool/edge may be used to cut into the adjacent bony structure such that the resulting cuts accommodate one or more struts of truss structure 1806. For example, where truss structure 1806 includes a triangular shape, such as that depicted in FIG. 18, one or more complementary cuts may be made into the adjacent bony structure in a complementary pattern. FIG. 19 illustrates a cut 1820 that may be made into adjacent bony structure 1822 prior to or as a result of truss structure 1806 being advanced/pressed into the adjacent bony structure 1822. FIG. 19 may be representative of an end view of a vertebra (e.g., looking upward/downward into the end plate of the vertebrae). In some embodiments, cut 1820 may include one or more segments intended to accommodate one or more struts of truss structure 1806. For example, in the illustrated embodiment, cut 1820 includes three slits 1820a,b,c formed in bony structure 1822. Slits 1820a,b,c may extend from the face of the boney structure into the bony structure in a direction substantially perpendicular to a face of the bony structure and/or substantially parallel to the intended direction of advancement of truss structure 1806 and/or implant 1800 into the bony structure.

In some embodiments, slits 1820a,b,c include cuts into the bone that do not require any boney material to be removed. For example, a sharp cutting edge may be advanced into the bone to create the slit, with no substantial amount of bone being removed. During implantation of implant 1800 into bony structure 1822, struts 1808a,b,c may slide into slits 1820a,b,c, respectively. Although the illustrated embodiments includes three slits oriented at approximately one-hundred twenty degrees relative to one another about a vertex 1824, other embodiments may include any number of slits in any variety of orientation to accommodate one or more struts of a truss structure extending from a contact face of an implant. Cut 1820 may be complementary to the shape/orientation of struts 1808 of truss structure 1806. For example, where truss structure is substantially pyramidal in shape (e.g., see truss structure 1806b described below with respect to FIG. 23), cut 1820 may include four slits oriented at approximately ninety-degrees relative to one another.

In some embodiments, cut 1820 may be formed by one or more complementary cutting members (e.g., knives/blades) that are pressed, slid, or otherwise advanced into boney structure 1822. In one embodiment, a cutting member includes one or more cutting edges arranged complementary to the profile of the struts of the truss structure such that advancement of the cutting edge cuts one, a plurality, or all of the slits to accommodate the truss structure being advanced/pressed into the bony structure.

Figure 20:
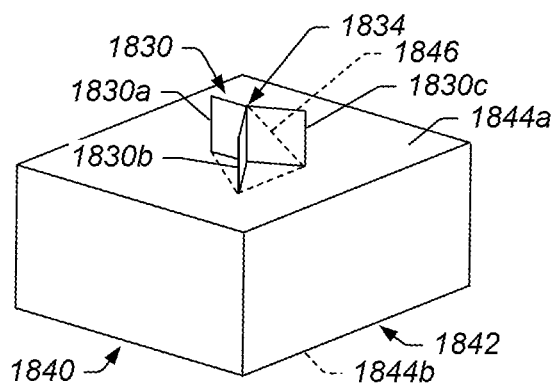
FIG. 20 illustrates a cutting member, according to an embodiment.

FIG. 20 illustrates a cutting member 1830 in accordance with one or more embodiments of the present technique. Cutting member 1830 includes three cutting blades 1830a,b,c oriented at approximately one-hundred twenty degrees relative to one another about a vertex 1834. In some embodiments, cutting members 1830a,b,c, are arranged complementary to slits 1820a,b,c of cut 1820 and/or struts 1808a,b,c of truss structure 1806. Although the illustrated embodiment includes three cutting blades oriented at approximately one-hundred twenty degrees relative to one another about a vertex 1834, other embodiments may include any number of cutting blades in any variety of orientation to accommodate one or more struts of a truss structure extending from a contact face of an implant. For example, where truss structure is substantially pyramidal in shape (e.g., see truss structure 1806*b* described below with respect to FIG. 23), cutting member 1830 may include four cutting blades oriented at approximately ninety-degrees relative to one another.

In some embodiments, the cutting blades may be advanced into boney structure 1822 at a depth that is about the same or deeper than the height of truss structure 1806. In some embodiments, the cutting blades may be advanced into boney structure 1822 at a depth that is about the same or shallower than the height of truss structure 1806. In some embodiments, a leading edge of the cutting blades may be shaped to be complementary to the shape of the struts. For example, the leading edge of one, a plurality, or all of cutting blades 1830*a,b,c*, may be angled similar to the angle of struts 1808*a,b,c* extending from contact surface 1804*a*, as illustrated by dashed line 1846.

In some embodiments, cutting member 1830 may be provided as an instrument that is advanced into the boney structure. In some embodiments, cutting member 1830 may be integrated with or more other devices used during the implantation procedure. For example, during a spinal implant procedure, cutting member 1830 may be coupled to a distractor typically positioned between the vertebrae and expanded to set the relative positions of the vertebrae. The force of distraction may act to advance the cutting member into the bony structure.

FIG. 20 illustrates a cutting member 1830 is disposed on a top surface 1844*a* of a body 1842 of a distractor 1840, in accordance with one or more embodiments of the present technique. In some embodiments, one or more cutting members may be disposed on other portions of distractor, such as a bottom surface 1844*b*. During use, distractor 1840 may be disposed between the adjacent bony structures and expanded such that top and bottom surfaces 1844*a,b* move away from one another, thereby pressing one or more of cutting members 1830 into the adjacent boney structure (e.g., 1822) to form one or more cuts (e.g., 1820) in the boney structure, where the cuts are intended to accommodate struts (e.g., 1808*a,b,c*) of the truss structure (e.g., e.g., 1806) of an implant (e.g., 1800) to be engaged with the boney structure. In some embodiments, the distractor may be used to increase a separation distance between two adjacent bony structures (e.g., between end plates of adjacent vertebrae). In some embodiments, subsequent to making the cuts, the distractor is unexpanded and/or removed, and the implant (e.g., 1800) is disposed between the bony structures (e.g., in substantially the same position as the distractor) such that one or more truss structures are aligned/engaged with one or more of the cuts.

Figure 21:
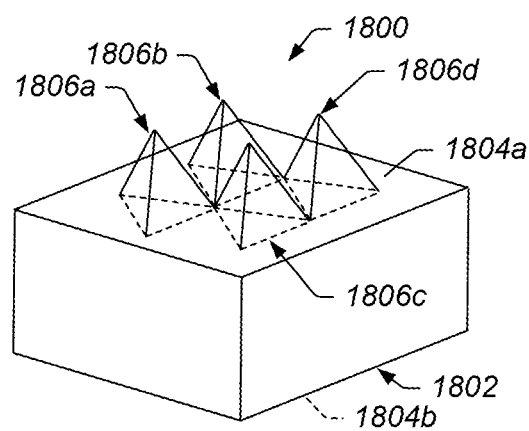
FIGS. 21-22 illustrate a plurality of truss structures disposed on an implant, according to an embodiment.

Although several of the above embodiments have been described with regard to a single truss structure, other embodiments may include any number of truss structures. For example, as depicted in FIG. 21, a plurality of truss structures may be provided on one or more contact surfaces of implant 1800. In the illustrated embodiment, four truss structures 1806*a,b,c,d* are disposed substantially adjacent one another on contact surface 1804*a,b* of implant 1800 such that one, a plurality, or all of struts of truss structures 1806*a,b,c,d* share common vertices at the contact surface 1804*a*. In some embodiments, one, a plurality or all of truss structures may be spaced apart from one another. For example, one, a plurality, or all of truss structures 1806*a,b, c,d* may not share a vertices at or near contact surface 1804*a*. In some embodiments, any number of truss structures may be provided on any portion of implant 1800. In some embodiments, the shape and orientation of the truss structures may be varied to mimic various desired shapes. For example, in some embodiments, the truss structures may be varied in height to provide a curved profile similar to that of a ball and/or a socket of a joint.

Figure 22:
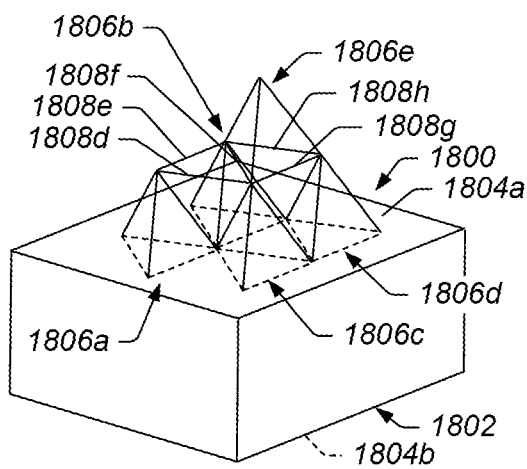

In some embodiments, implant 1800 may include a plurality of truss structures stacked upon one another to form a web-like structure disposed on one or more faces of implant 1800. FIG. 22 illustrates a multi-layer truss-structure (e.g., web structure) disposed on a contact surface of implant 1800 in accordance with one or more embodiments of the present technique. In the illustrated embodiment, a triangular truss structure 1806*e* is stacked atop vertices of truss structures 1806*b,c,d*. In some embodiments, a truss structure provided at a contact surface of an implant may include a web structure, such as those described with respect to implants 100, 200 250, 600 and 650 described herein. In some embodiments, the shape and orientation of the web structures may be varied to mimic various desired shapes. For example, in some embodiments, the web structure may be varied in height to provide a curved profile similar to that of a ball and/or a socket of a joint.

In some embodiments, one or more additional struts may be provided between one, a plurality, or all of the vertices of truss structures. For example, in the illustrated embodiment, struts 1808*d,e,f,g,h* extend between the vertices of truss structures 1806*a,b,c,d*. In some embodiments, one or more struts may extend between a plurality or all of the struts at or near the point where they are coupled to the contact face. For example, one or more struts may extend in place of one or more of the dashed lines illustrated in FIGS. 18, 21, 22 and 23.

Figure 23:
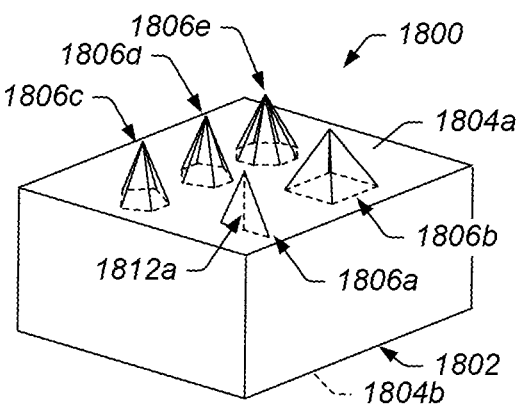
FIG. 23 illustrates various types of truss structures disposed on an implant, according to an embodiment.

Some of the above embodiments have been described with respect to a particular shaped truss structure (e.g., a triangular shaped space truss structure 1806) although various shapes of truss structures are contemplated. It will be appreciated that such description is intended to be exemplary and is not intended to be limiting. FIG. 23 illustrates a plurality of exemplary truss structures that may be coupled to a contact face of an implant in accordance with one or more embodiments of the present technique.

In some embodiments, a truss structure 1806 may include a triangular-shaped planar truss. For example, truss structure 1806*a* includes two substantially shaped truss members extending from contact surface 1804*a* and coupled to one another at a vertex to define an open region 1812*a* through which bone growth may occur. Other embodiments may include any variety of geometrical truss structure shapes, such as four-sided (e.g., pyramidal), five-sided, six-sided, seven sided (not depicted), and/or eight sided truss structures 1806*b,c,d,e*, respectively. Additionally, cubic, rectangular or pentagonal block shaped structures may be used. Moreover, embodiments may include any of the truss-structures disclosed herein, such as those disclosed with respect to FIGS. 1A-9. In some embodiments, any type, size, number, or combination of number, types and sizes of truss structures may be provided on one, a plurality, or all of the contact faces of an implant.

Figure 24:
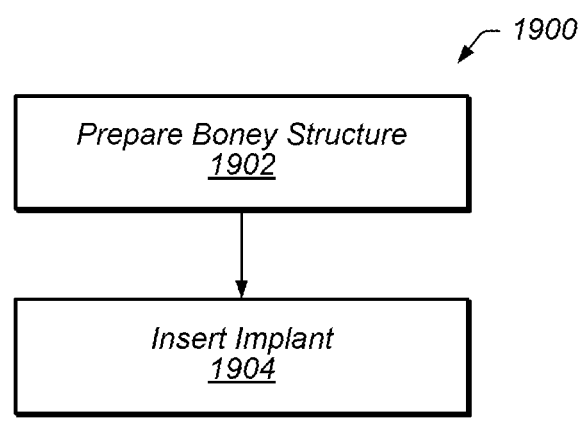
FIG. 24 is a flowchart that illustrates a method of implanting an implant, according to an embodiment.

FIG. 24 is a flowchart that illustrates a method 1900 of implanting an implant in accordance with one or more embodiments of the present technique. In the illustrated embodiment, method 1900 includes preparing a boney structure, as depicted at block 1902, and inserting an implant (e.g., 1800), as depicted at block 1904. In some embodiments, preparing a boney structure includes positioning the boney structure. For example, a distractor (e.g., 1840) may be used to separate adjacent boney structures such that the implant can be sandwiched between the two adjacent boney structures. In some embodiments, preparing a boney structure includes cutting/slitting the boney structure to accommodate one or more struts of a truss structure of an implant to be coupled to the boney structure. For example, a cutting member (e.g., 1830) may be advanced into the boney structure to create a cut (e.g., 1820) including one or more slits (e.g., 1820a,b,c). In some embodiments, distraction and cutting may be provided simultaneously via use of a distractor that includes one or more cutting members coupled to one or more of its contact faces (e.g., distractor 1830 having cutting members 1830 coupled thereto).

In some embodiments, inserting the implant includes positioning the implant (e.g., 1800) adjacent the boney structure (e.g., 1822), aligning the truss structure (e.g., 1806) with a complementary portion of the boney structure (e.g., 1820) and/or advancing a contact surface (e.g., 1804a,b) toward the boney structure such that at least the truss structure is in contact or near contact with the boney structure. In some embodiments, the implant may be advanced until the contact surface is in contact or near contact with the boney structure, such that at least portion or substantially all of the truss structure is disposed in the boney structure. For example, substantially all of the struts of the truss structure may be disposed in the slits provided in the boney structure.

As will be appreciated, method 1900 is exemplary and is not intended to be limiting. One or more of the elements described may be performed concurrently, in a different order than shown, or may be omitted entirely. Method 1900 may include any number of variations. For example, in some embodiments, struts 1806 may include a sharp/thin profile such that minimal preparation of the boney structure needed (e.g., cuts do not need to be provided in the boney structure) as the struts of the truss structure may, pierce the boney structure as the implant is advanced into contact with the boney surface. Accordingly, in some embodiments, steps 1902 and 1904 of method 1900 may be combined into a single step.

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

In accordance with the above descriptions, in various embodiments, an implant may include a web structure. The web structure for the implant may include a micro truss design. In some embodiments, the micro truss design may include a web structure with multiple struts. Other web structures are also contemplated. The web structure may extend throughout the implant (including a central portion of the implant). The web structure may thus reinforce the implant along multiple planes (including internal implant load bearing) and provide increased area for bone graft fusion. The web structure may be used in implants such as spinal implants, corpectomy devices, hip replacements, knee replacements, long bone reconstruction scaffolding, and cranio-maxifacial implants. Other implant uses are also contemplated. In some embodiments, the web structure for the implant may include one or more geometric objects (e.g., polyhedrons). In some embodiments, the web structure may not include a pattern of geometrical building blocks (e.g., an irregular pattern of struts may be used in the implant). In some embodiments, the web structure may include a triangulated web structure including two or more tetrahedrons. A tetrahedron may include four triangular faces in which three of the four triangles meet at each vertex. The web structure may further include two tetrahedrons placed together at two adjacent faces to form a web structure with a hexahedron-shaped frame (including six faces). In some embodiments, multiple hexahedron-shaped web structures may be arranged in a side-by-side manner. The web structures may connect directly through side vertices (e.g., two or more hexahedron-shaped web structures may share a vertex). In some embodiments, the web structure may be angled to provide lordosis to the implant.

Further modifications and alternative embodiments of various aspects of the invention may be apparent to those skilled in the art in view of this description. For example, although in certain embodiments, struts have been described and depicts as substantially straight elongated members, struts may also include elongated members curved/arched along at least a portion of their length. Accordingly, this description is to be construed as illustrative only and is for the purpose of teaching those skilled in the art the general manner of carrying out the invention. It is to be understood that the forms of the invention shown and described herein are to be taken as embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims. Furthermore, it is noted that the word "may" is used throughout this application in a permissive sense (i.e., having the potential to, being able to), not a mandatory sense (i.e., must). The term "include", and derivations thereof, mean "including, but not limited to". As used in this specification and the claims, the singular forms "a", "an" and "the" include plural referents unless the content clearly indicates otherwise. Thus, for example, reference to "a strut" includes a combination of two or more struts. The term "coupled" means "directly or indirectly connected".

What is claimed is:

1. An implant for interfacing with a bone structure, comprising:
    an external frame defining an exterior surface of the implant, and
    an internal space truss structure at least partially enclosed by the external frame comprising two or more planar truss units comprising a plurality of struts joined at nodes, wherein at least two nodes within the internal space truss structure are connected by a strut that curves or arcs between the at least two nodes, and wherein at least one of the two or more planar truss units lies in a plane that is not substantially parallel to a plane of at least one or more of the other two or more planar truss units;
    wherein at least a portion of the internal space truss structure extends into a central portion of the implant.

2. The implant of claim 1, wherein the internal space truss structure comprises at least one strut that passes through a central portion of the implant.

3. The implant of claim 1, wherein the external frame comprises at least one of a top, a bottom, or a side portion of the implant.

4. The implant of claim 1, wherein the external frame comprises one or more planar trusses that each comprise two or more planar truss units disposed proximate an exterior of the internal space truss structure.

5. The implant of claim 1, wherein the external frame comprises two or more planar trusses adjacent one another, wherein each of the two or more adjacent planar trusses comprise two or more adjacent planar truss units that lie in substantially the same plane.

6. The implant of claim 1, wherein the internal space truss structure comprises a plurality of truss units in the shape of pyramids, and wherein at least two of the pyramids are arranged opposing one another such that they share a square shaped common planar truss unit at their base to form an octahedron.

7. The implant of claim 1, wherein the implant is configured for use as a spinal implant, a corpectomy device, in a hip replacement, in a knee replacement, in a long bone reconstruction scaffold, foot and ankle implant, shoulder implant, a joint replacement or in a cranio-maxifacial implant.

8. The implant of claim 1, wherein at least one of the struts of the internal space truss structure comprises a biologic, growth factor or antimicrobial coupled thereto.

9. The implant of claim 1, wherein at least one of the nodes is located in the central portion of the implant.

10. The implant of claim 9, wherein at least some of the curved or arced struts connect to the at least one node in the central portion.

11. A method, comprising:
accessing a space proximate a bone structure comprising human bone tissue; and
inserting an implant into the space, wherein the implant comprises:
an external frame defining an exterior surface of the implant, and
an internal space truss structure at least partially enclosed by the external frame comprising two or more planar truss units comprising a plurality of struts joined at nodes, wherein at least two nodes within the internal space truss structure are connected by a strut that curves or arcs between the at least two nodes, wherein at least one of the two or more planar truss units lies in a plane that is not substantially parallel to a plane of at least one or more of the other two or more planar truss units, wherein at least a portion of the internal space truss structure extends into a central portion of the implant.

12. The method of claim 11, wherein the space comprises an intervertebral space and, wherein the implant comprises a spinal fusion implant.

13. The method of claim 11, wherein the space comprises a void proximate an ankle or knee, and wherein the implant comprises an osteotomy implant.

14. The method of claim 11, wherein the internal space truss structure comprises at least one strut that passes through the central portion of the implant.

15. The method of claim 11, wherein the external frame comprises at least one of a top, a bottom, or a side portion of the implant.

16. The method of claim 11, wherein the external frame comprises one or more planar trusses that each comprise two or more planar truss units disposed proximate an exterior of the internal space truss structure.

17. The method of claim 11, wherein the external frame comprises two or more planar trusses adjacent one another, wherein each of the two or more adjacent planar trusses comprise two or more adjacent planar truss units that lie in substantially the same plane.

18. The method of claim 11, wherein the internal space truss structure comprises a plurality of truss units in the shape of pyramids, and wherein at least two of the pyramids are arranged opposing one another such that they share a square shaped common planar truss unit at their base to form an octahedron.

19. The method of claim 11, wherein at least one of the struts of the internal space truss structure comprises a biologic, growth factor or antimicrobial coupled thereto.

20. The method of claim 11, wherein at least some of the curved or arced struts connect to at least one node in the central portion of the implant.

* * * * *